(12) United States Patent
Harvie

(10) Patent No.: US 11,026,829 B2
(45) Date of Patent: Jun. 8, 2021

(54) HYDRO-BLOCK AIR VENT COMBINATION CATHETER SYSTEM AND METHOD OF USE

(71) Applicant: Mark Harvie, Williston, VT (US)

(72) Inventor: Mark Harvie, Williston, VT (US)

( * ) Notice: Subject to any disclaimer, the term of this patent is extended or adjusted under 35 U.S.C. 154(b) by 307 days.

(21) Appl. No.: 16/153,730

(22) Filed: Oct. 6, 2018

(65) Prior Publication Data

US 2019/0038451 A1  Feb. 7, 2019

Related U.S. Application Data

(63) Continuation-in-part of application No. 14/794,787, filed on Jul. 8, 2015, now abandoned, and a continuation-in-part of application No. 14/270,467, filed on May 6, 2014, now Pat. No. 9,788,992.

(51) Int. Cl.
| | |
|---|---|
| *A61F 5/441* | (2006.01) |
| *A61M 25/00* | (2006.01) |
| *A61F 5/453* | (2006.01) |
| *A61F 5/455* | (2006.01) |
| *A61M 1/00* | (2006.01) |
| *A61M 25/02* | (2006.01) |

(52) U.S. Cl.
CPC .............. *A61F 5/441* (2013.01); *A61F 5/453* (2013.01); *A61F 5/455* (2013.01); *A61M 25/0017* (2013.01); *A61M 1/0025* (2014.02); *A61M 1/0066* (2013.01); *A61M 25/0043* (2013.01); *A61M 2025/0213* (2013.01); *A61M 2025/0266* (2013.01); *A61M 2202/0496* (2013.01); *A61M 2205/3379* (2013.01)

(58) Field of Classification Search
CPC .. A61M 2205/3379; A61M 2202/0496; A61M 2025/0266; A61M 25/0017; A61M 1/0025; A61M 1/0066; A61M 25/0043; A61M 2025/0213; A61F 5/453; A61F 5/441; A61F 5/455–4556; A61F 5/451
See application file for complete search history.

(56) References Cited

U.S. PATENT DOCUMENTS

| | | | |
|---|---|---|---|
| 4,656,675 A * | 4/1987 | Fajnsztajn | A61F 5/453 |
| | | | 4/144.3 |
| 4,889,533 A * | 12/1989 | Beecher | A61F 5/4405 |
| | | | 604/330 |

(Continued)

*Primary Examiner* — Susan S Su
(74) *Attorney, Agent, or Firm* — Eric R. Benson, Esq.

(57) ABSTRACT

This invention is a device utilizing hydro-block venting material in various external male and female catheter configurations permitting adequate airflow into the catheter thereby permitting efficient and complete drainage of urine away from the user following urination. In two embodiments user's expelled urine is automatically detected by a sensor and drawn away from the user by a pump means to a user selected storage means as a pressure relief balloon prevents air interference with the sensor. In another embodiment gravity is utilized to draw user's expelled urine away from user to a user selected storage means. An adhesive, garment or strap attachment means are disclosed as attachment means to secure the external male and female catheter to user and prevent leakage. The external male and female catheters are engineered to also be able to be connected to and used in combination with an indwelling catheter.

8 Claims, 15 Drawing Sheets

(56) References Cited

U.S. PATENT DOCUMENTS

| | | | | |
|---|---|---|---|---|
| 5,306,226 | A | * | 4/1994 | Salama ................. A61F 2/0009 128/DIG. 25 |
| 9,788,992 | B2 | * | 10/2017 | Harvie .................... A61F 5/455 |
| 2015/0196730 | A1 | * | 7/2015 | O'Callaghan ..... A61M 25/0017 604/544 |

* cited by examiner

HYDRO-BLOCK AIR VENT COMBINATION CATHETER SYSTEM AND METHOD OF USE

CROSS REFERENCE TO RELATED APPLICATION

This Application is a Continuation-In-Part of the patent application U.S. Ser. No. 14/794,787, filed Jul. 8, 2015, which in turn is a Continuation-In-Part of the patent application U.S. Ser. No. 14/270,467, filed May 6, 2014 (Now U.S. Pat. No. 9,788,992), which claimed priority from Provisional Patent Application No. 61/819,833 which was filed on May 6, 2013. This application also claims priority from the Provisional Patent Application No. 62/041,894.

BACKGROUND ART

The English word "catheter" comes from the Greek word kathienai, meaning "to let or send down." The historical and archaeological record teaches that catheters were used as early as 3,000 B.C.E. principally to relieve the pain of urinary retention. Ancient doctors used many different materials to form a hollow catheter shape which included: reeds of straw, rolled up palm leaves, the hollow tops of onions, gold, silver, copper, brass, and yes, even lead. The 11th century C.E. saw the advent of the malleable catheter. Eventually in later centuries silver was in more common use principally because it could be bent to a desired shape and was believed to have an antiseptic function. The antimicrobial properties of silver have been known to cultures all around the world for many centuries. The Phonecians stored water and other liquids in silver coated bottles to discourage contamination by microbes. In fact Benjamin Franklin invented a silver catheter for use by his brother who suffered from kidney stones and who needed to undergo the daily placement of his brother's bulky silver catheter into his bladder. To make this less painful Franklin designed a flexible catheter, albeit still of silver. Franklin is quoted as saying about his catheter that "[i]t is as flexible as would be expected in a thing of the kind, and I imagine will readily comply with the turns of the passage."

The invention of rubber vulcanization by Goodyear® in 1844 not only improved the firmness of the catheter it dramatically increased the durability as well. The vulcanized rubber Coudé tip catheter was developed and in common use in the late 18th and early 19th centuries principally to provide for male catheterization and these types of male catheters continue to be used in current medical practice today. Because the catheters during this time period were made from rubber they proved to be very weak at body temperature and caused serious health concerns. The catheter would break down and leave debris in the bladder that led to serious complications, not the least of which was bladder infections. Another major problem for these indwelling catheters was holding them in place. The earliest self retaining catheters had Malecot wing tips or Pezzer flexible shoulders that were tied to the male penis or sutured to the female labia to maintain the catheter in a functional position.

The invention of latex rubber and that of neoprene by Dupont™ in the early 1930s solved many significant problems that were being experienced with the vulcanized rubber indwelling catheters. The first artificial sphincter designed as an inflatable circular cuff was created by Frederic Foley in 1947. Foley is best known for the improvement of the principles of the transurethral indwelling balloon catheter and he played a major role in the introduction of commercially manufactured indwelling balloon catheters in the 1930s. The Foley catheter is widely used in multiple health care settings to this day.

The concept of sterile intermittent catheterization in patients with spinal cord injury was first introduced after World War II. Dr. Jack Lapides while at the University of Michigan at Ann Arbor introduced the clean intermittent catheterization technique in 1971. Despite the fact that sterile technique had been used for catheterization for many years, urinary tract and bladder infections were frequent occurrences among patients that had been catheterized. Lapides concluded that bacteria were not the only cause of infections among these patients. He first posited the accepted conclusion that chronic stagnant urine residuals and overstretching of the bladder are also responsible for these infections. Although Lapides was criticized in the medical community regarding his conclusions he held fast to his conclusion that sterile intermittent catheterization was superior to indwelling catheters. More than four decades later the clean intermittent catheterization recommended by Lapides remains the preferred method to treat chronic urine retention and a neurogenic bladder.

The indwelling or intermittent catheterization of the bladder has historically been viewed as safe because of the antiseptic methods of use and manufacture that have become common practice. From the beginning up to today, however, many physicians are very concerned about catheter related infections. Countless patients are still developing systemic infections (catheter fever) despite the use of antiseptic methods of manufacture and use.

It has become fairly standard medical protocol for the treatment of patients to keep internal catheters placed for as long as they remain unable to use a bathroom facility. This sadly results in frequent and severe bladder or urinary track infections. These hospital-acquired infection (HAI) or nosocomial infections are infections whose developments are favored by a hospital environment. These nosocomial infections have been determined to affect approximately five percent of hospitalized patients. These infections are very painful and can often lead to disability, longer hospital stays and even death. Worldwide the treatment of indwelling catheter generated nosocomial infections costs the healthcare system billions of dollars each year. In fact, indwelling catheter generated hospital-acquired infections account for as much as forty percent of all nosocomial infections.

It is commonly known in the art and the healthcare industry that there are several problems that are common with the use of indwelling catheters such as the Foley catheter. Some of these problems have been identified as:
   The balloon can break while the catheter is being inserted.
   The balloon might not inflate after it is in place.
   Urine stops flowing into the bag.
   Urine flow is blocked.
   The urethra begins to bleed.
   Introduction of an infection into the urethra and/or the bladder. The risk of infection in the bladder or urinary tract increases with the number of days the catheter is in place.
   If the balloon is opened before the Foley catheter is completely inserted into the bladder, bleeding, damage and even rupture of the urethra may occur. In some individuals, long-term permanent scarring and strictures of the urethra may occur.
   Defective catheters may be supplied, which break in place. The most common fractures occur near the distal end or at the balloon.

Catheters can be pulled out by patients while the balloon is still inflated, leading to major complications or even death.

The balloons fail to deflate for removal and while be being pulled out when the balloon is still inflated also leads to major complications or even death.

To prevent leakage and maximize the functionality of the catheters, the catheters are sized to fit snugly in the urethra of a user which is not of a uniform and placement in such tight conditions causes irritation and often damage to the urethra.

Virtually all indwelling catheters leak around the catheter which increases the risk of infection and causes extreme discomfort to the catheterized patient.

The medical community appears to have concluded that the incidents of indwelling catheter generated nosocomial infections can be reduced, if not eliminated, with an effective external catheter being used in place of an indwelling device for incontinent patients. The problem for the medical community is that very few such external collection devices have been developed in the art and none of them afford an effective solution to this chronic problem. Additionally an external catheter is not an effective device for patients suffering from urinary retention or ischuria for which an indwelling catheter is still the treatment of choice.

Prior Art Female External Catheters.

In view of these problems there have been a number of attempts in the prior art female external catheters to solve these problems. The prior art teaching these devices appear in U.S. Pat. No. 3,601,125 to Moss; U.S. Pat. No. 4,233,978 to Hickey; U.S. Pat. No. 4,563,183 to Barrodale; and U.S. Pat. No. 4,615,692 to Giacalone. Some of the prior art teach a device that has a projection adapted for insertion into the vagina itself such as found in U.S. Pat. No. 3,776,235 to Ratcliffe; U.S. Pat. No. 4,194,308 to Anderson; U.S. Pat. No. 4,198,979 to Cooney; said U.S. Pat. No. 4,563,183; and said U.S. Pat. No. 4,615,692. U.S. Pat. No. 3,349,768 to Keane also attempts to solve these problems with a portable urinal with a suction means designed to fit a female patient. The interface with the female genitalia has a suction head designed to receive a removable pad of open celled porous material.

Additionally, U.S. Pat. No. 4,202,058 teaches a female urinal that utilizes a lined receptacle with an attached drainage tube that can be connected to a pump and the tube is comprised of of a corrugated or cellulose portion with one way valves at each end to provide suction for removing urine from the urinal portion of the device. U.S. Pat. No. 4,246,901 teaches a urine collection device that is funnel shaped and filled with a wicking material to soak up discharged urine.

A multiple layer absorbent pad is taught in U.S. Pat. No. 4,360,015. Two layers of absorbent material in this device are separated by a grid material and are covered on one side by a moisture permeable layer and on the other side by an impermeable layer. This absorbent methodology is also taught in U.S. Pat. No. 4,798,603 where the absorbent material is made up of a substantially hydrophilic material with a facing and a liquid permeable top sheet layer of hydrophobic material. The device also has a liquid permeable transport layer placed between the top sheet and the absorbent material that is made of a material less hydrophobic than the patient's body.

U.S. Pat. No. 4,747,166 is a liquid aspiration system that includes an absorptive pad with an inner core of urine absorbing material, an upper pad facing layer of liquid permeable hydrophobic material in contact with the user and a lower pad backing of impermeable material. The pad has a flexible perforated tube with a liquid outlet connector at one end. The device has a vacuum or pump, a urine collection means and vacuum tubing coupling the tube within the pad to the collection means and the vacuum or pump. The vacuum or pump may run continuously or be activated by a sensor in the pad.

U.S. Pat. No. 4,631,061, is an automatic urine detecting, collecting and storing device with a urine collection means that has sensors for detecting the presence of urine which then activates a pump to draw urine from the collection means to a storage means.

U.S. Pat. No. 4,610,675, is a female urine collection device that is a flexible pad with an elongated central opening for partial vaginal insertion within the external area of the genitalia. The absorbent core has a plurality of layers of material.

U.S. Pat. No. 4,981,474, teaches a urine drainage device that has a wedge shaped reservoir with hinged sidewalls that are joined along a common edge with a collapsible sidewall. Spring inside the device hold the hinged sidewalls apart and inlet and outlet ports with a one way valve to facilitate the flow of urine.

U.S. Pat. No. 4,886,508 teaches an external catheter assembly for women which has a panty support for proper placement of the collection means. The panty and the collection means cooperate such that the urine collection means' position can be adjusted relative to the panty to optimize comfort and function.

Again the problem with all of these female external catheters or urine collection systems is that they are only appropriate for use by an incontinent person and not for bladder management of a person suffering with urinary retention or ischuria for which indwelling catheterization remains the only effective means of bladder management.

Prior Art Male External Catheters. The use of external catheters, i.e. the condom or Texas catheter for treating male urinary incontinence is well known, as disclosed in U.S. Pat. Nos. 4,378,018, 4,187,851, 3,863,638, 3,835,857 and 4,475,910, however the use of male external catheters is only appropriate for use by an incontinent person and not for bladder management of a person suffering with urinary retention or ischuria for which indwelling catheterization remains the only effective means of bladder management. These external urinary drainage means or condom catheters first appear in the patent literature in German Pat. No. 520.401. These condom catheters are typically comprised of an elastic sheath adapted to fit over the penis. The sheath is manufactured with an outlet at its distal end that can be connected to a tube or other collection means. The sheath is typically designed with a constricted downstream end portion adapted for fluid-tight connection with a drain tube. The sheath is usually comprised of a thin elastomeric fluid-impermeable material such as latex rubber or silicone rubber. This sheath is for all intents and purposes similar to a condom which can be rolled onto the penis.

The prior art teaches several attachment means for condom catheters to the penis which include non adhesive and adhesive catheters. Non-adhesive condom catheters are held in place with either an inflatable ring such as the Cook Non-Adhesive Silicone Condom Catheter or a Velcro strap that can be wrapped around the sheath. These types of condom catheters are typically reusable.

The most popular condom catheter in use today are the one piece self-adhesive condom catheters. These condom catheters are easier to put on by rolling it over the shaft of the penis and then by pressing the catheter against the skin to help the adhesive to stick to the penis. Recent condom catheters are typically made entirely of silicone since it has been reported that these types of condom catheters are less likely to cause skin irritation or cause other adverse reactions. These of course are a good alternative for those in men with a latex allergy or sensitivity. A variation of these types of one piece condom catheters is the current art AlphaDry condom catheter which consists of a one way valve and a small reservoir that can be stored in a user's underwear.

Also available in the current art are two piece condom catheters which consist of a sheath and separate hydrocolloid strips. These hydrocolloid strips have adhesive surfaces on both the inside and outside. The hydrocolloid strips are first wrapped around the penis. The condom catheter is then rolled up the penis toward the abdomen over the strips and once unrolled it is then pressed to stick against the hydrocolloid strips that is adhered to the penis. A significant problem exists with this type of condom catheter because many users apparently will put on the strips in a way that is too tight for the penis causing irritation, restriction of blood flow and in some extreme cases, necrosis.

The Liberty Pouch™ is a small external flower shaped wafer that is applied and sealed to the penis tip. The Liberty Pouch™ is made of a hydrocolloid material and covered by a second layer of material that wraps around the glans or head of the penis for protection. The outside of the Liberty Pouch™ is designed to direct expelled urine into a tube for collection in a bag typically stored in the underwear or pants of a user. The Liberty Pouch™ is beneficial for men with either a short or retracted penis and also for un-circumcised men. The foreskin of the un-circumcised penis is retracted to allow application of the device and then brought forward to cover it. There are a large variety of external pouch types of condom catheters available. Because these pouch type condom catheters typically are adhered directly to the skin a user needs to remove the pubic hair surrounding the base of the penis often resulting in skin irritation.

It is well known in the art that using external condom catheters can cause a variety of serious problems for the user. These problems include skin irritation, maceration of the penis tip, urinary tract infections (UTI), ischemia and penile edema or urethral obstruction. Many of these complications occur frequently when the catheter: is not put on correctly; is used for longer than recommended; causes skin to be constantly wet which often softens the skin which eventually will be worn away by the condom catheter. Skin barrier products are often used prior to the application of the condom catheter to protect the skin from constant wetness but these have proven to be ineffective in preventing these potentially life threatening conditions.

The use of adhesive straps, especially with the condom catheters with adhesive on both sides, is known to cause strangulation of the penis or to excessively constrict it. Condom catheters are also known to cause infections which typically stems from the fact that all current art condom catheters are ineffective in preventing urine from accumulating and remaining against the penis and often times the urethra. Current art condom catheters are designed to prevent leakage of urine but at the same time they also prevent air from reaching the skin which would permit the urine to drain and prevent anaerobiosis of urinary tract infectious agents. The skin of a user can also break down with minor erosion and dermatitis resulting from lack of air and presence of urine.

It has been suggested that clear silicone condom catheters allow a user to see their skin condition while they are worn and also allow some oxygen and water vapor to reach the skin. This is largely anecdotal and would depend upon the fit of the condom catheter. Even with more rigid clear silicone condom catheters the buildup of urine occurs especially if the condom catheter fits more snuggly on the penis.

Backflow leakage is a persistent problem in condom catheters as well resulting from fluid backflow between the penis and the sheath of the condom. In an attempt to resolve this problem the prior art teaches the interposing of a sealant pad between the sheath and the penis as disclosed in U.S. Pat. Nos. 4,187,851, 4,378,018. The consequences of the backflow of urine are well known, urinary tract infections, sores, discomfort and other related problems. Sealant pads are designed to prevent leakage and to retain the catheter in place. It is well known in the art that there are significant problems with this design in fitting these pads and catheters on the penis exactly as intended. The pad depicted in U.S. Pat. No. 4,187,851 for example is comprised of an adhesive strip intended to be wrapped around the penis before the condom catheter is unrolled into position. This process is difficult if not impossible for most patients suffering from urinary incontinence since they often lack the ability to undertake such intricate maneuvers. Attending medical personnel are often unable or unwilling to take the time necessary for properly wrapping and molding the sealant pads in place, and then carefully fitting the sheaths over the pads to form the necessary leak proof seal. Additionally the problems that may result from the improper application of such a condom catheter often are more serious than backflow leakage or patient discomfort, i.e. urinary tract infections and sores. In the event an adhesive pad as shown in U.S. Pat. No. 4,187,851 is wrapped too tightly around the penis, circulation might be impaired and tissue necrosis could result.

Condom catheters are also available with an internal coating of pressure sensitive adhesive eliminating the need for using a separate adhesive-coated sealant pads, as depicted in U.S. Pat. No. 4,475,910. This composition does appear to avoid some of the serious dangers that have been associated with the wrap around sealant pads described above, however, the known difficulties of applying these types of condom catheters coupled with the problem of leakage resulting from improper application persist and they may even be worse. Inordinate care is necessary when unrolling these types of adhesive coated condom catheters over the penis to make certain that the condom catheter is evenly applied without wrinkles or flow channels. Making matters worse many users while trying to handle these condom catheters frequently experience the adhesive coated inner surface coming into contact with each other and sticking together during application of the catheter. Separation of these surfaces after they have stuck together is virtually impossible. The result often prevents any corrective steps being taken and leakage of the condom catheter is for all intents and purposes a certainty.

U.S. Pat. No. 4,589,874 teaches the use of a condom catheter that has an inner sleeve designed to be stretched about the glans of the penis to prevent backflow and protect the delicate skin from injury that may be caused by long-term contact with residual urine that may remain near the outlet end of the sheath when the catheter is used. Whether these catheters are held in place by adhesive coating or an adhesive pad, they all require for proper placement of the inner sleeve into a fluid-tight contact with the glans portion of the penis before the proximal portion of the condom catheter may be adhesively secured to the penis. Again, this is a major difficulty in the use of these types of condom catheters and consequently are particularly unpopular.

Attempts have been made as shown in the prior art to try and resolve the backwash effect by introducing various means of removing accumulated urine by various means such as wicking fibers. For instance U.S. Pat. No. 4,820,289 discloses a condom catheter flocked with particles of fiber. This disclosed flocked external condom catheter is comprised of a sheath adapted to fit over the penis with a constricted downstream end portion adapted for a fluid-tight connection with a drain tube. One of the surfaces disclosed in this patent is comprised of a thin layer of adhesive and a uniform layer of small particles of a bonded fabric.

Other prior art patents of generally relating to condom catheters are U.S. Pat. Nos. 4,022,213, 4,284,079, 3,405,714, 4,239,044, 3,353,538, 3,511,241, 3,721,243, 3,631,857, 3,788,324, 3,339,551, 3,364,932, 4,296,502, and 3,742,953.

The prior art condom catheters, while partially effective in aiding male suffering with incontinence, as disclosed above, each have a number of significant problems such as:

1) Attachment by adhesive which is difficult to obtain an effective seal without channeling issues occurring and causing a serious skin irritation and damage upon removal for many users;
2) Difficulty in applying and removing the condom catheter without injuring the penis;
3) Difficulty in securely attaching the condom catheter to a user such that it remains functional, despite activity and a flaccid condition of the penis; and
4) Accumulation of urine that causes irritation and urinary tract and other types of infections.

Again the problem with all of these male external catheters or urine collection systems is that they are only appropriate for use by an incontinent person and not for bladder management of a person suffering with urinary retention or ischuria for which indwelling catheterization remains the only effective means of bladder management.

It is known in the art that most complications that occur with both male and female external catheters occur when the catheter is either used incorrectly or used for a longer period of time than intended. The most common complications that can occur are:

Skin irritation or urinary tract or bladder infections.
Constant wet skin can become soft and worn away by the external catheter.
Allergic reactions to the materials can develop as well.

All of the prior art above does not effectively permit urine to escape the initial collection area thus leaving a user wet with their own urine. This is so even when a vacuum or pump means is utilized to draw urine away from the user because the materials used in the primary collection area adjacent to the urethra do not provide an adequate venting means to permit the urine to completely evacuate and the area to dry.

Prior Art Combination Catheters.

An extensive search of the prior art reveals that there are no devices available or even taught for bladder management that combine an effective external urine collection system or catheter with an indwelling catheter. Further there are no indwelling catheters that effective and sanitary in use unless the catheter is sized to fit relatively snugly inside the urethra.

Thus, while there are a number of prior art attempts to solve the problem of patients remaining wet while wearing these devices and developing infections, etc., none of these devices are satisfactory solutions. Therefore there is a great need for a combination catheter device that is easily donned and remains securely in place regardless of the activity level of the user. Furthermore, to solve the problems of the prior art devices this combination catheter must also effectively facilitate the aspiration of backwashed urine that may accumulate between the genitalia and the catheter that is unable to drain from the distal or discharge end of the catheter. Similarly there is a need for a combination catheter system that combines an external catheter or urine collection means with an indwelling catheter, thereby eliminating the necessity of using an indwelling catheter that is large enough to fit snugly in the urethra which is a leading cause of urethral damage and infection. Because my invention utilizes an effective external urine collection and management means the indwelling catheter does not have to fit snugly within the urethra thereby virtually eliminating the damage caused by friction and trauma caused by catheter placement of the larger catheters. My invention also utilizes a connection means between the external catheter component and the indwelling catheter that completely eliminates the need for a balloon to hold the indwelling catheter in place. The elimination of the need for a balloon solves all of the problems listed above that stem from such indwelling devices that utilize balloons in placement. My invention is designed to solve these problems that exist in the current art.

DISCLOSURE OF THE INVENTION

Purpose of Invention

The purpose of the invention is to provide a combination catheter that will permit a user to use the device solely as an external catheter or as a combination external catheter and indwelling catheter. The external catheter portion of the device will permit air to enter into the device by means of a Hydro-block or similar substance air vent that allows air to flow into the external component of the catheter system while blocking the urine from exiting except through the distal end drain as intended. The external catheter component of the combination catheter system is designed also to collect urine that may exit the urethra of a person that is also using the indwelling catheter component of my invention. Because my invention utilizes an effective external urine collection and management means the indwelling catheter does not have to fit snugly within the urethra thereby virtually eliminating the damage caused by friction and trauma caused by catheter placement of larger catheters. My invention also utilizes a connection means between the external catheter component and the indwelling catheter that completely eliminates the need for a balloon to hold the indwelling catheter in place. The elimination of the need for a balloon solves all of the problems listed above that stem from such indwelling devices that utilize balloons in placement. This invention will allow the urine to completely drain out of the combination catheter and the hose and completely away from the user's skin.

Description of Problems Solved by Invention

There are currently no combination catheter devices. There are currently no external or indwelling catheter devices that will fit a user securely enough to allow for reasonable physical activity of a user that will also permit air to enter into the external catheter and thereby allow any backwashed urine to escape, thereby preventing such adverse medical conditions as skin irritation, maceration of the genitalia, urinary tract infections (UTI), ischemia and edema or urethral obstruction. The current invention incorporates a proprietary Hydro-block air vent that allows air to flow into the external catheter while blocking the urine from exiting except through the distal end intended drain. This invention will allow the urine to completely drain out of the external catheter and any attached hose and ultimately away from the user's skin, unlike current art external catheters which permit urine to accumulate and remain in contact with the user's skin and urethra.

My combination catheter invention incorporates into the external catheter component a proprietary Hydro-block air vent that allows air to flow into the catheter while blocking the urine from exiting. This invention will allow the external catheter component for female use to be very small in size, only a few millimeters deep and wide, allowing for a unique and multiple sizing for each female anatomy. The small size makes it possible for females to wear the system under normal clothing while hydro block air filters allow the catheter to drain completely under gravity in most positions. Similar benefits are realized by male users with the external condom catheter component of my invention. Also with the addition of my patented bladder relief sensor activated pump (U.S. Pat. No. 7,866,942), the urine is completely drained out of the external catheter away from the user's skin leaving them dry at all times no matter what physical orientation their body is in, (i.e. standing, walking, climbing, sitting, reclined, lying flat on back, raised legs or in a hospital bed, lying on either side, lying on stomach in fact even upside down). This will result in significant reduction in skin ulcers, maceration and UTI which are currently all major problems and are a significant cost to the healthcare system for inpatient hospital care, nursing home long term care and most importantly home health care resulting in significant reduction in complications and wound care caused by urinary incontinence. By combining an indwelling catheter component to this combination catheter system a person suffering from urinary retention or ischuria may have a smaller sized indwelling catheter placed that will not irritate or damage the urethra because the indwelling catheter does not have to fit snugly in the urethra, nor does the indwelling catheter have to have a balloon to hold it in place in the bladder because the indwelling catheter component is held in place by being functionally connected to the external catheter component. Any urine that may leak around the indwelling catheter is collected in and drained from the external catheter component of the combination catheter device.

The most critical function of the invention disclosed in these letters patent is the aeration of the external catheter component of the device and the smaller sized indwelling catheter portion of the device that is smaller than the prior art and stays in place without a balloon. There are a number of attachment means in the art for external catheters. Therefore it would be obvious to one skilled in the art for example to use an adhesive, garment or strap types of attachment means to hold my invention with the Hydro-block or similar substance air vent in place.

Brief Description of Invention

My invention is a combination catheter system which incorporates a proprietary Hydro-block or similar substance air vent that allows air to flow into the external catheter component while blocking the urine from exiting except through the intended drainage site at the distal end of the external catheter component. Incontinent users typically would only need to use the external catheter component of my invention, however, if a user is bed ridden or suffering from urinary retention or ischuria such a user would use the indwelling catheter component in combination with the external catheter component of my invention. The indwelling catheter component of this system is of a size smaller than the urethra of a user such that the indwelling catheter may more easily be inserted into the urethra and into the bladder of a user without damaging the urethra in the process. The indwelling catheter component of this system is attached to the external catheter component of this device which thereby holds the catheter in place thus eliminating the need of a balloon to hold the indwelling catheter in place in the user's bladder. This invention in either configuration will allow the urine to completely drain out of the system and any attached hose and ultimately away from the user's skin.

BEST MODES FOR CARRYING OUT THE INVENTION

I. Preferred Embodiments

Figure 21:
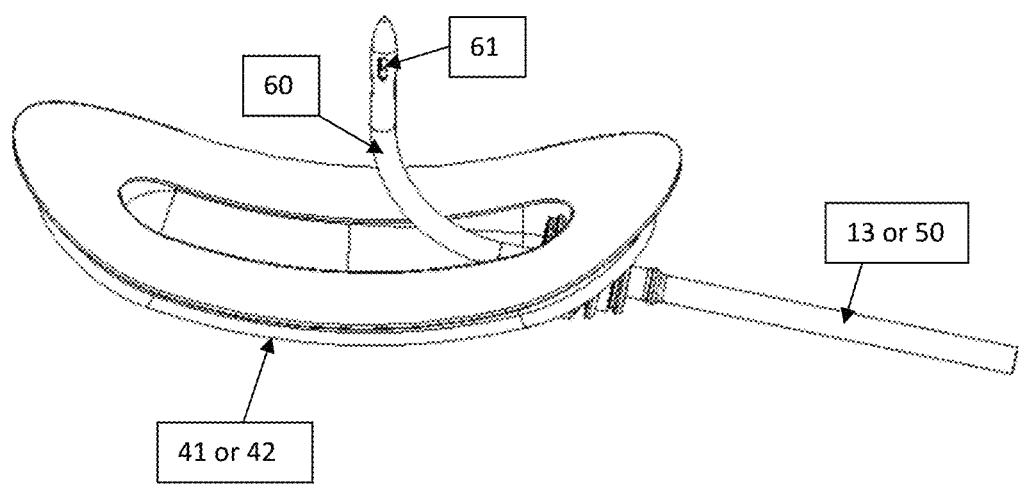
FIG. 21 is a side perspective view of the Indwelling Catheter used in both male and female combination embodiments with the Indwelling Catheter Connector attached completely inserted into the Hydro-Block Air Vent Female External Catheter with the Drain Tube attached.
Figure 22:
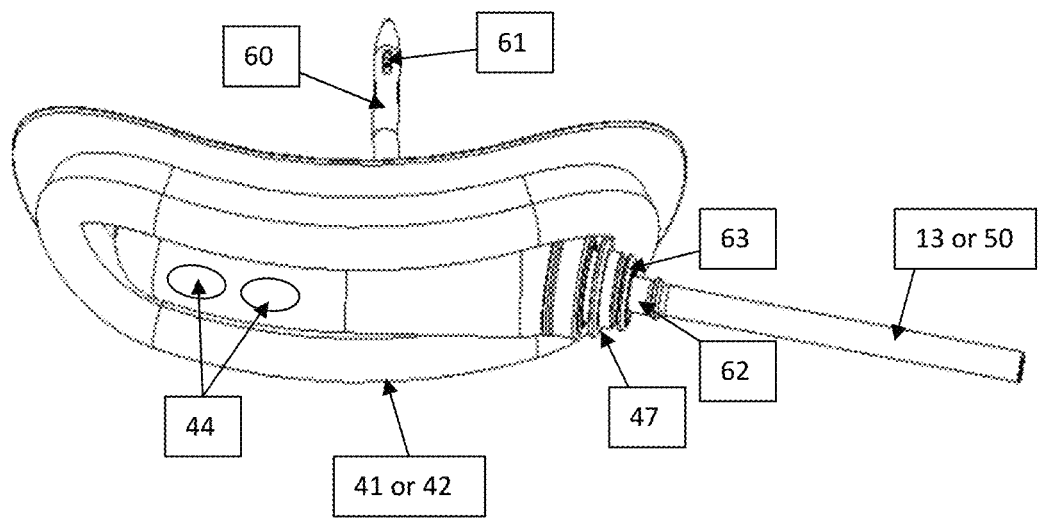
FIG. 22 is a bottom side perspective view of the Indwelling Catheter used in both male and female combination embodiments with the Indwelling Catheter Connector attached completely inserted into the Hydro-Block Air Vent Female External Catheter with the Drain Tube attached and further depicting the Hydro-block Air Intake Vent, Hydro-block Air Intake Coupler and the Indwelling Catheter Connector.
Figure 23:
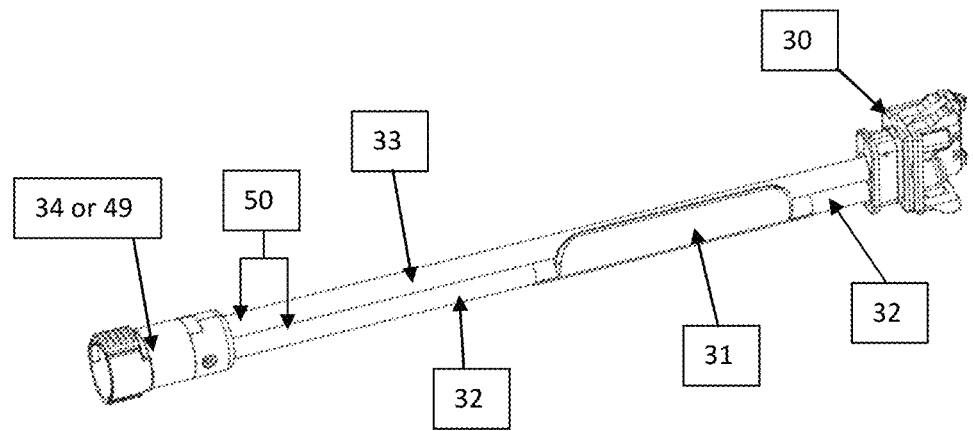
FIG. 23 is a side perspective view of the drainage and sensor connections of both the male and the female urine collection assemblies with the pump and storage means for all embodiments that utilize automatic sensors with a pumping means with the pressure relief balloon in a collapsed state.
Figure 23A:
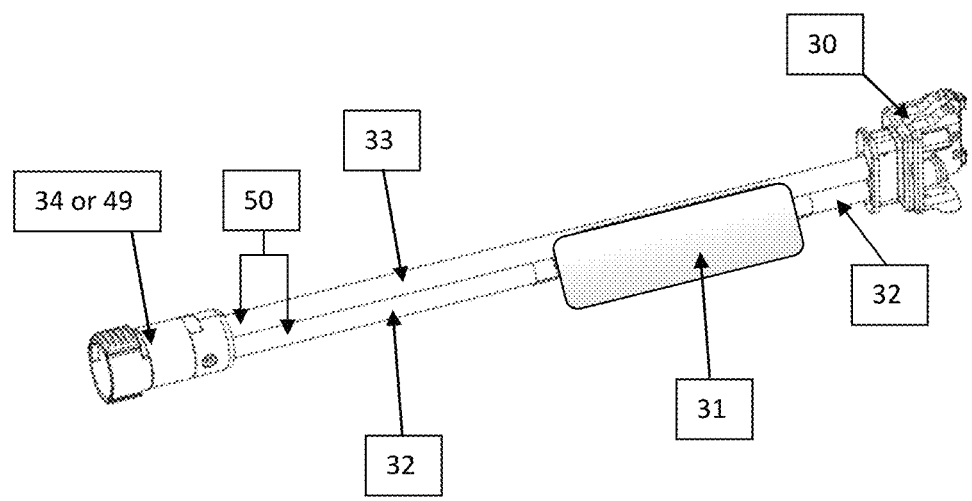
FIG. 23A is a side perspective view of the drainage and sensor connections of both the male and the female urine collection assemblies with the pump and storage means for all embodiments that utilize automatic sensors with a pumping means with the pressure relief balloon in its expanded state during a user's urination.

With reference now to the drawings, and in particular to FIGS. 1-23A thereof, are depicted a Combination Catheter System which is engineered to allow a user to combine a new and novel external catheter component (one male and one female) with an indwelling catheter component. The external component and the indwelling catheter component can each be used separately from the other depending upon the bladder management needs of the user. FIGS. 1-5 depict two embodiments of a new and novel external female catheter utilizing hydro-block technology. FIGS. 6-15 depict four embodiments of a new and novel condom catheter utilizing hydro-block technology. FIGS. 16-20 depict a new and novel male combination embodiment of an indwelling catheter with a condom catheter utilizing hydro-block technology. FIGS. 21-22 depict a new and novel female combination embodiment of an indwelling catheter with an external female catheter utilizing hydro-block technology. FIGS. 23-23A depict a new and novel fluid and sensor connection system from a urine collection means to a pumping and storage means that utilizes a pressure relief balloon to prevent air pockets or air bubbles from interfering with the fluid sensors within the device.

Figure 1:
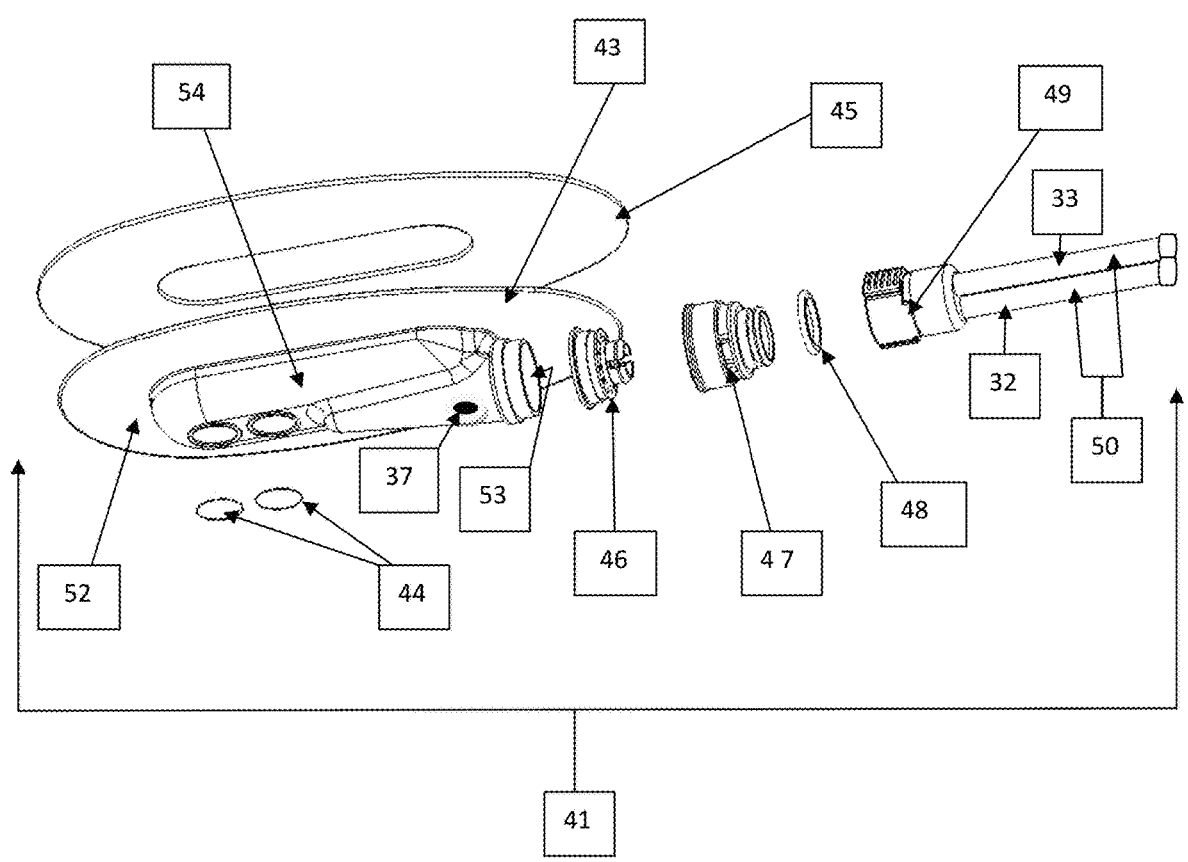
FIG. 1 is an exploded perspective side view of the pump draining embodiment of the Hydro-Block Air Vent Female External Catheter.

FIG. 1 depicts the Pump Draining embodiment of the Hydro-Block Air Vent External Female Catheter (41) which has at least one Urine Sensor (37) disposed in the Micro Collection Chamber (54) which is in electronic communication with a pump means to draw expelled urine from the Hydro-Block Air Vent External Female Catheter (41) to a user selected storage or disposal means. The Pump Draining embodiment of the Hydro-Block Air Vent External Female Catheter (41) is further comprised of Hydro-Block Air Intake Vents (44).

Figure 2:
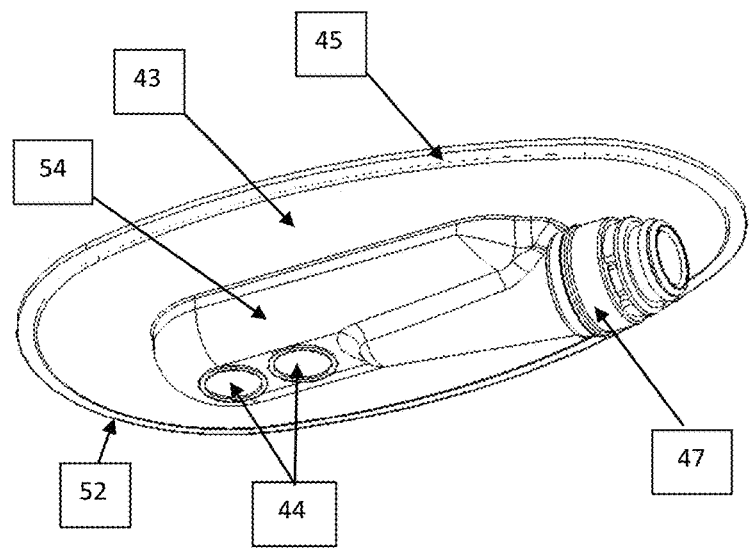
FIG. 2 is a perspective side view of the gravity draining embodiment of the Hydro-Block Air Vent Female External Catheter without the Quick Disconnect Coupling and Drainage Hose attached.
Figure 3:
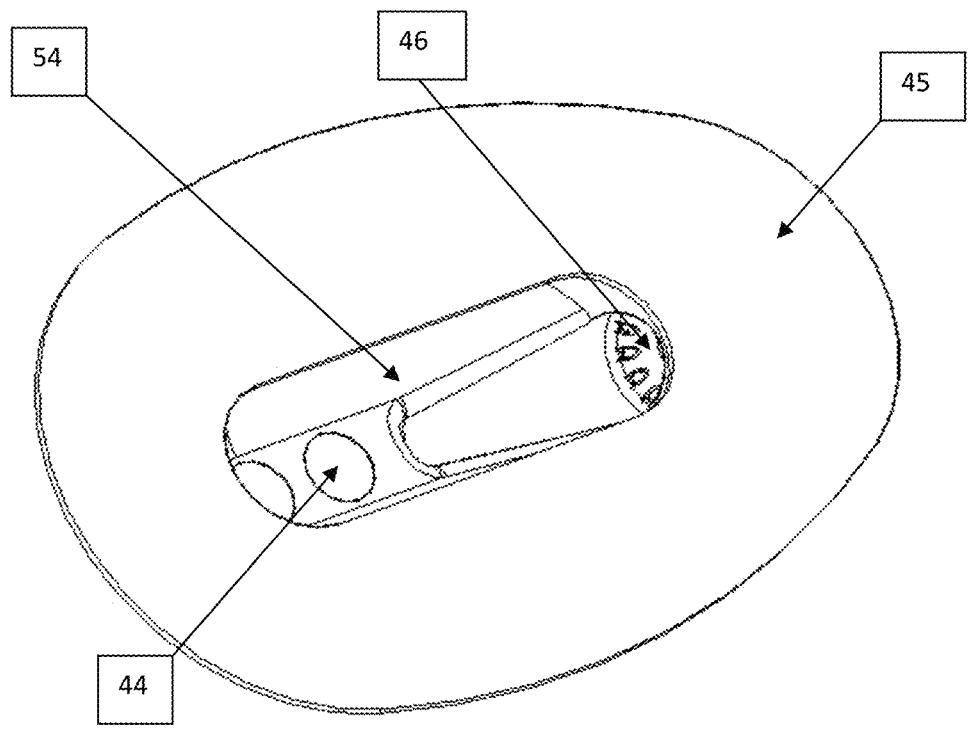
FIG. 3 is a perspective side view of the gravity draining embodiment of the Hydro-Block Air Vent Female External Catheter without the Hydro-block Air Intake Coupler, Quick Disconnect Coupling and Drainage Hose attached.

FIGS. 2 and 3 depict the Gravity Draining embodiment of the Hydro-Block Air Vent External Female Catheter (42) together with the Hydro-Block Air Intake Vents (44), but without the device's drainage components connected to the device.

Figure 2A:
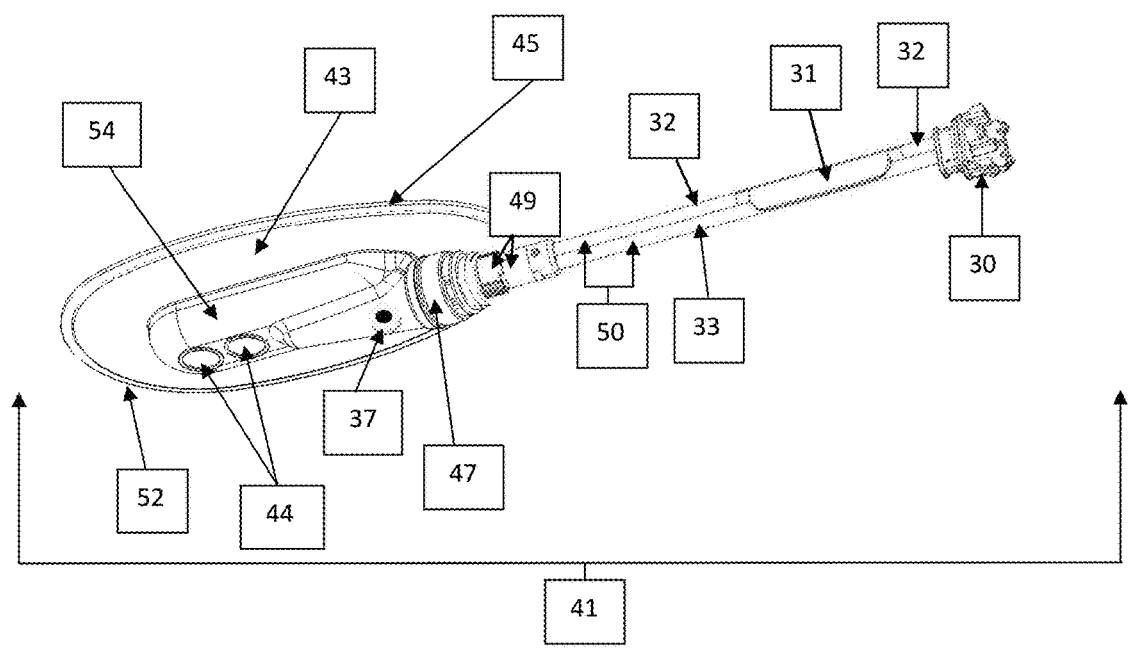
FIG. 2A is an perspective side view of the pump draining embodiment of the Hydro-Block Air Vent Female External Catheter with the drainage components connected to the device including a pressure relief balloon in its collapsed state prior to urination commencement by a user.

FIG. 2A depicts the Pump Draining embodiment of the Hydro-Block Air Vent External Female Catheter (41) of FIG. 1 together with the drainage components connected to the device including the Pressure Relief Balloon (31) in its collapsed state prior to urination commencement.

Figure 4:
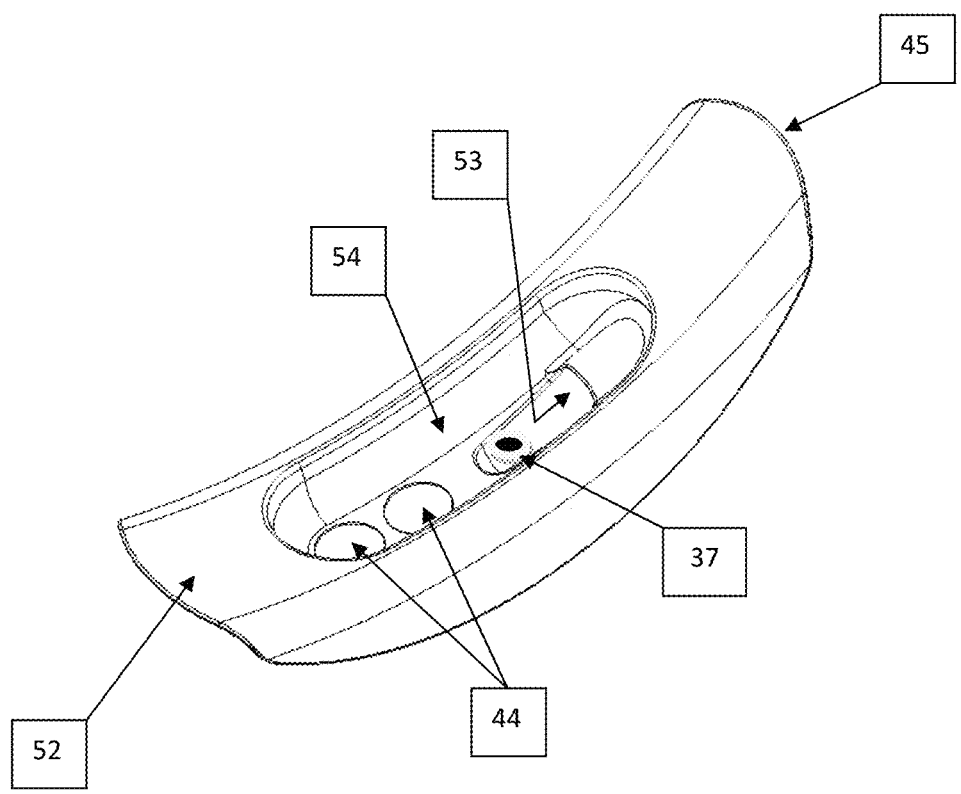
FIG. 4 is a right side perspective top view of the pump draining embodiment of the Hydro-Block Air Vent Female External Catheter depicting the urine collection area of the Micro Collection Chamber.

FIG. 4 depicts the Pump Draining embodiment of the Hydro-Block Air Vent External Female Catheter (41) with the Urine Sensor (37) disposed in the Micro Collection Chamber (54) together with the Hydro-Block Air Intake Vents (44), but without the device's drainage components connected to the device.

Figure 5:
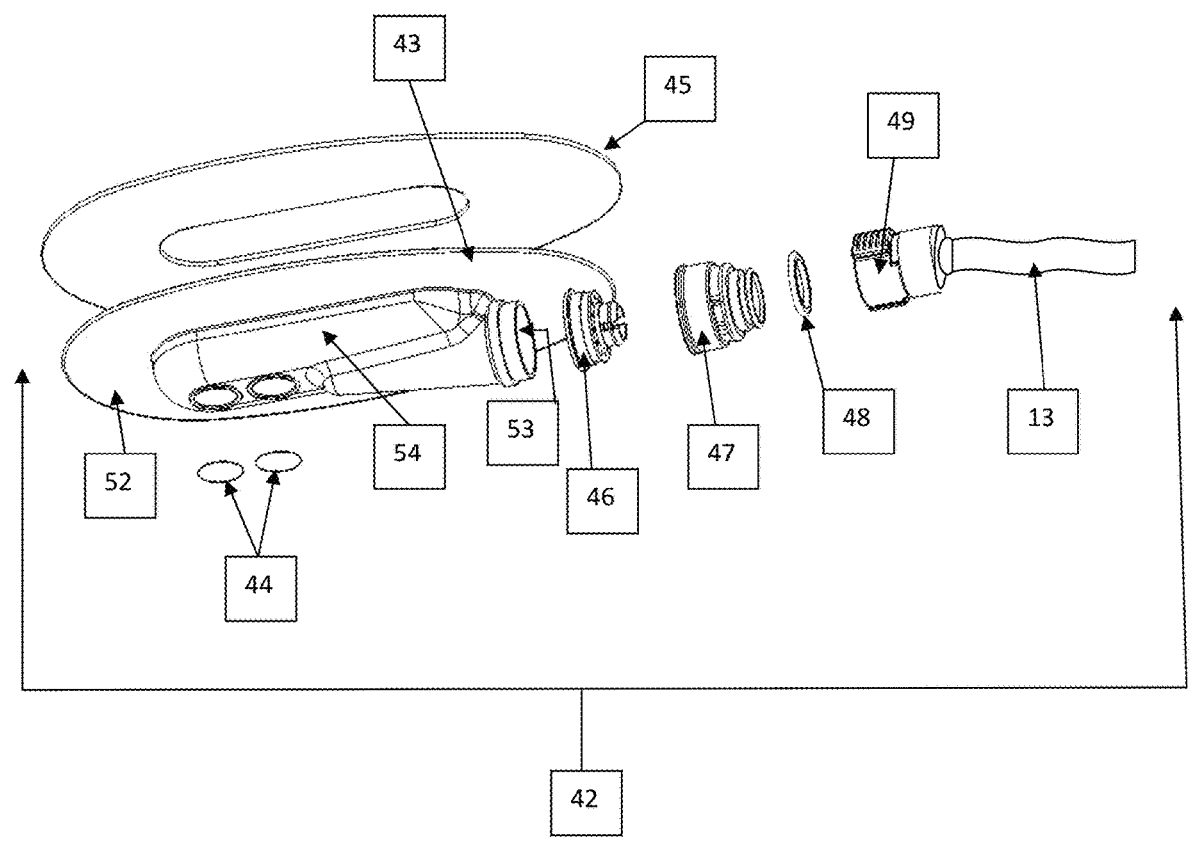
FIG. 5 is an exploded perspective side view of the gravity draining embodiment of the Hydro-Block Air Vent Female External Catheter.

FIG. 5 depicts the Gravity Draining embodiment of the Hydro-Block Air Vent External Female Catheter (42) which utilizes gravity to draw expelled urine from the Hydro-Block Air Vent External Female Catheter (42) to a user selected storage or disposal means. The Gravity Draining embodiment of the Hydro-Block Air Vent External Female Catheter (42) is further comprised of Hydro-Block Air Intake Vents (44).

Figure 6:
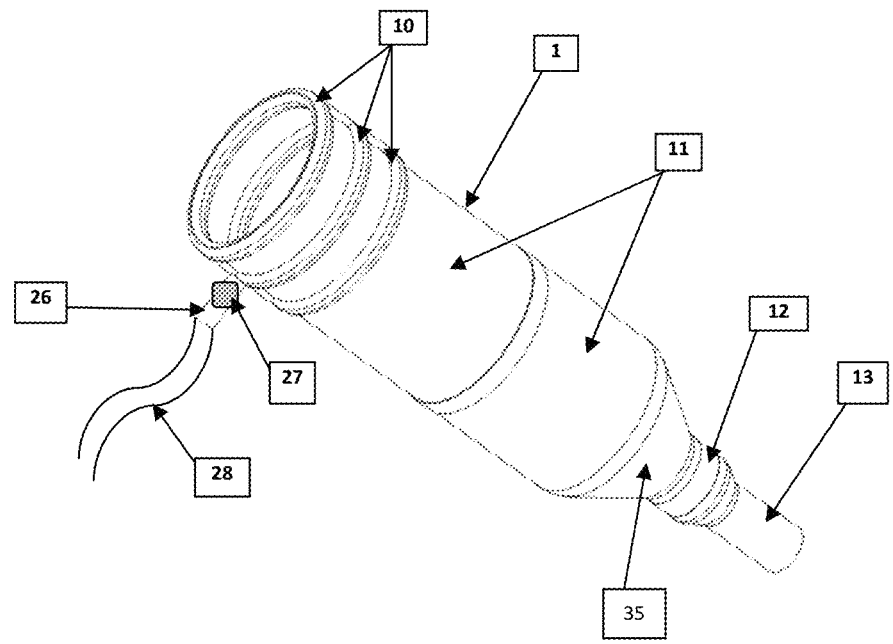
FIG. 6 is a proximal-side perspective view of the Hydro-Block Air Vent Condom Catheter with Inflatable Rings.

FIG. 6 depicts the Inflatable Ring embodiment of the Hydro-Block Air Vent Condom Catheter (1) which has a plurality of Inflatable Rings (10) disposed around the device to aid in maintaining the device securely sealed on a user's penis wherein the Hydro-Block Air Vent Condom Catheter (1) is comprised of Hydro-Block Air Vent (11).

Figure 7:
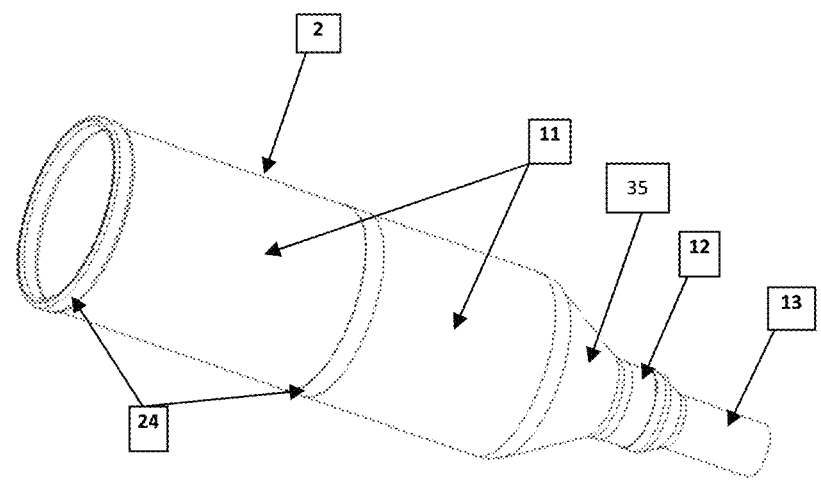
FIG. 7 is a proximal-side perspective view of the Hydro-Block Air Vent Condom Catheter without Inflatable Rings.

FIG. 7 depicts the Adhesive Ring embodiment of the Hydro-Block Air Vent Condom Catheter (2) which has a plurality of Adhesive Rings (24) disposed around the device to aid in maintaining the device securely sealed on a user's penis wherein the Hydro-Block Air Vent Condom Catheter (1) is comprised of Hydro-Block Air Vent (11).

Figure 8:
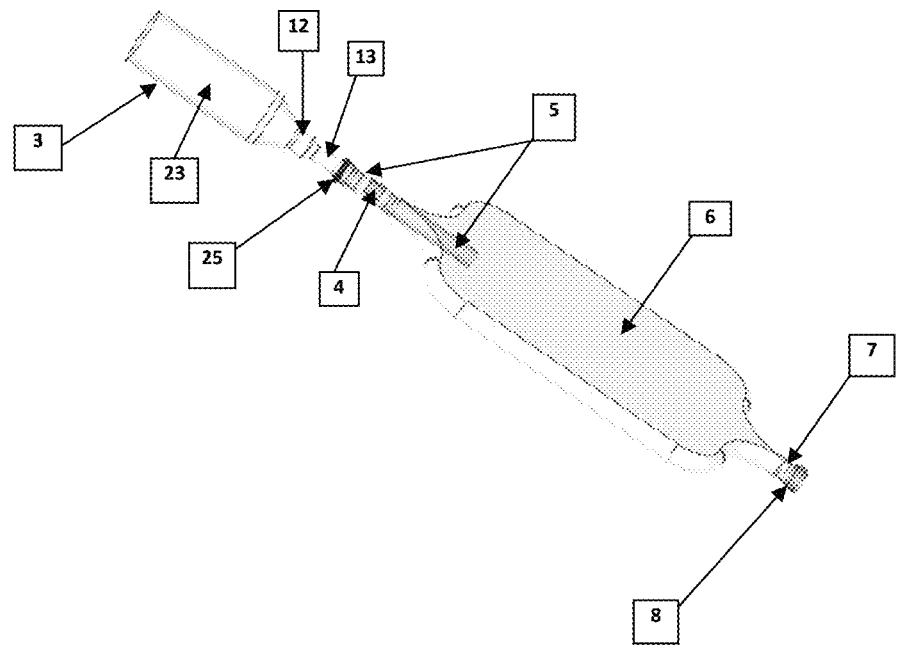
FIG. 8 is a proximal-side perspective view of the Hydro-Block Air Vent Condom Catheter without Inflatable Rings connected by a Hose to a Collections Bag.
Figure 9:
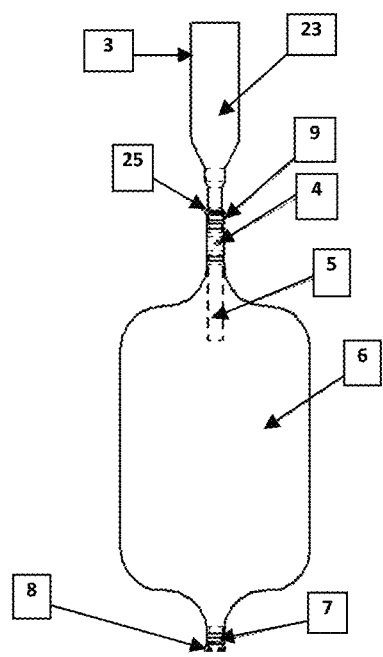
FIG. 9 is a front perspective view of the Hydro-Block Air Vent Condom Catheter without Inflatable Rings connected by a Hose to a Collections Bag.

FIGS. 8 and 9 depict the Storage Bag Venting embodiment of the Hydro-Block Air Vent Condom Catheter (3) which vents air for proper drainage of the device by means of a Storage Bag Hydro-Block Air Vent (4) attached to the proximal end of a Storage Bag (6).

FIGS. 10, 11, 12 and 13 depict the Retro Fit Embodiment of the Hydro-Block Air Vent Condom Catheter (22) which utilizes a Retro-Fit Assembly (21) that may be used with any condom catheter on the market today.

Figure 14:
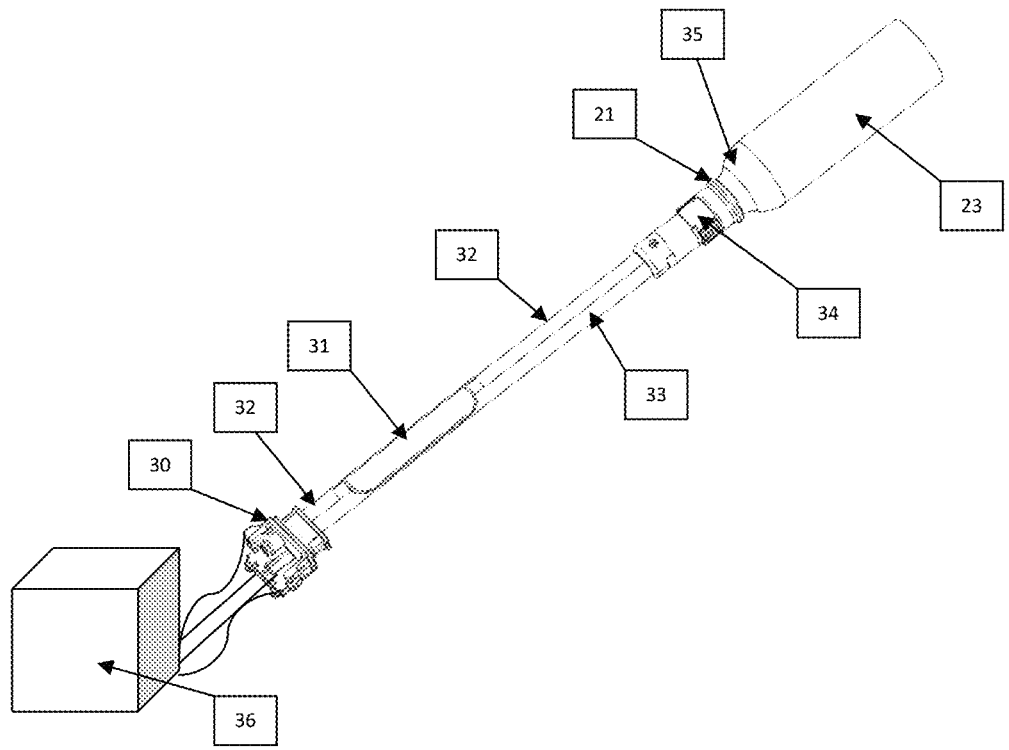
FIG. 14 is a proximal end perspective view of the assembled modified Retro-Fit Embodiment Hydro-Block Air Vent Condom Catheter configured with a quick disconnect hose system with pump connectivity and automatic urine sensing for pump activation.
Figure 15:
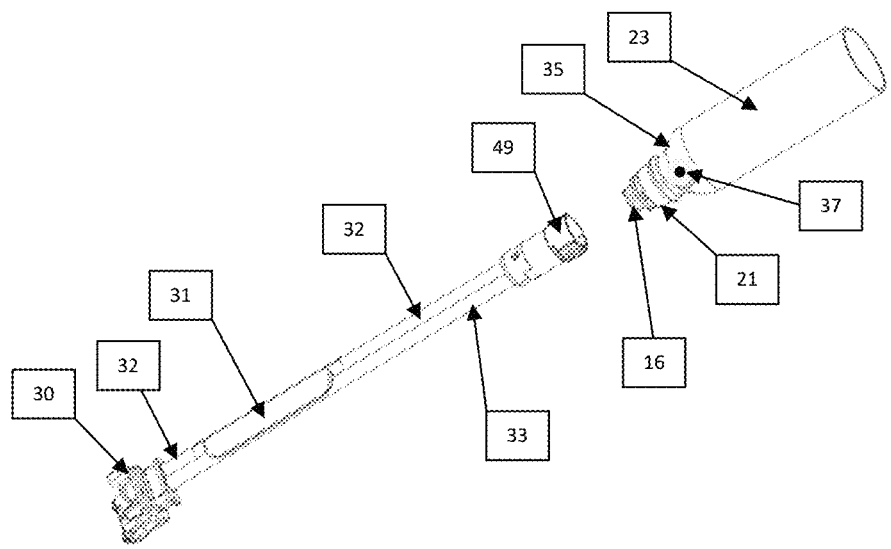
FIG. 15 is a proximal end exploded perspective view of the disassembled modified Retro-Fit Embodiment Hydro-Block Air Vent Condom Catheter configured with the quick disconnect hose system with pump connectivity and automatic urine sensing for pump activation disconnected from the condom portion of the device.

FIGS. 14 and 15 depict a modified Retro Fit Embodiment of the Hydro-Block Air Vent Condom Catheter (22) of FIGS. 7 and 8 wherein the Drain Tube (13) has been substituted with a quick disconnect system with pump connectivity and urine sensing to activate a pump comprised of a Pump and Sensor Connector (30), a Pressure Relief Balloon (31), a Liquid Hose (32), a Sensor Hose (33), and Quick Disconnect with Urine Sensor (34).

Figure 16:
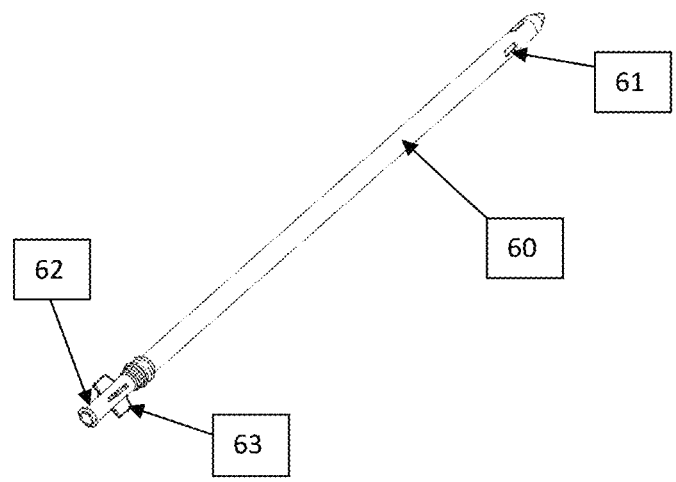
FIG. 16 is a side perspective view of the Indwelling Catheter used in both male and female combination embodiments with the Indwelling Catheter Connector attached.
Figure 17:
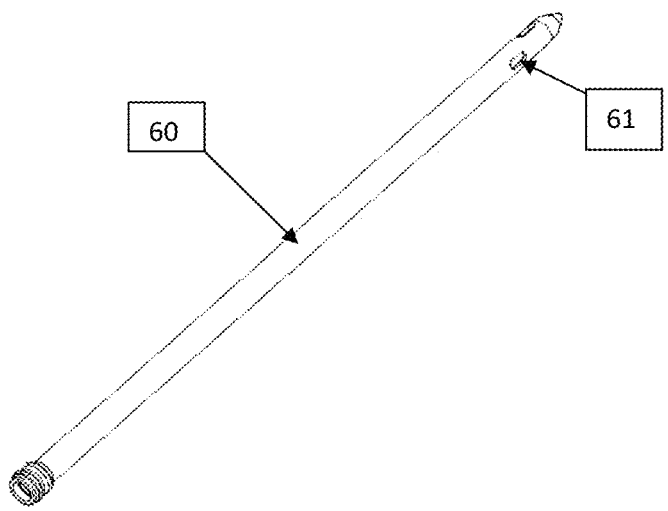
FIG. 17 is a side perspective view of the Indwelling Catheter used in both male and female combination embodiments without the Indwelling Catheter Connector attached.

FIGS. 16 and 17 depict the Indwelling Catheter (60) with a series of Indwelling Catheter Urine Ports (61) and an Indwelling Catheter Connector (62) with attached Indwelling Catheter Connector Spacer Wings (63).

Figure 18:
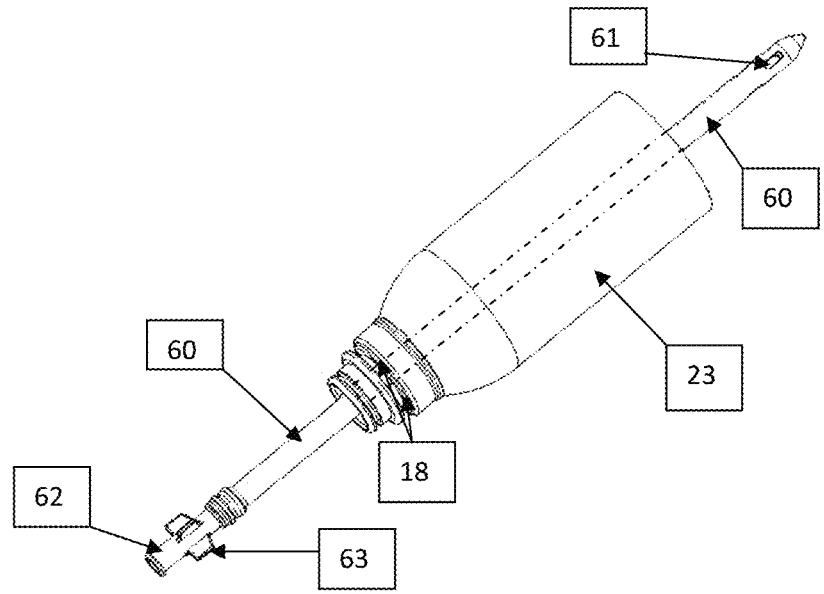
FIG. 18 is a side perspective view of the Indwelling Catheter used in both male and female combination embodiments with the Indwelling Catheter Connector attached being inserted into the Hydro-Block Air Vent Condom Catheter.
Figure 19:
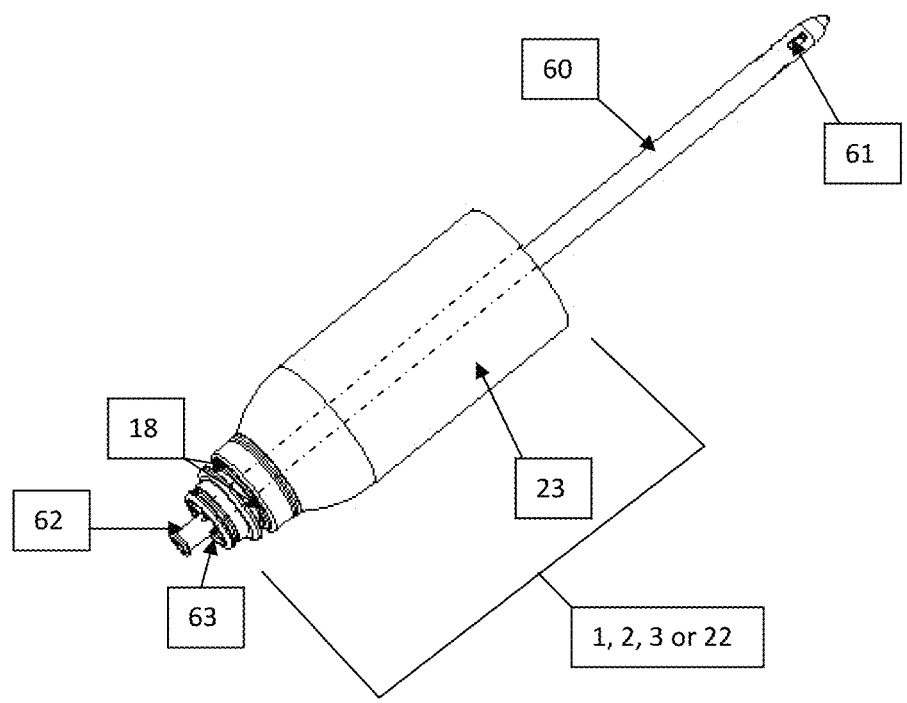
FIG. 19 is a side perspective view of the Indwelling Catheter used in both male and female combination embodiments with the Indwelling Catheter Connector attached completely inserted into the Hydro-Block Air Vent Condom Catheter.
Figure 20:
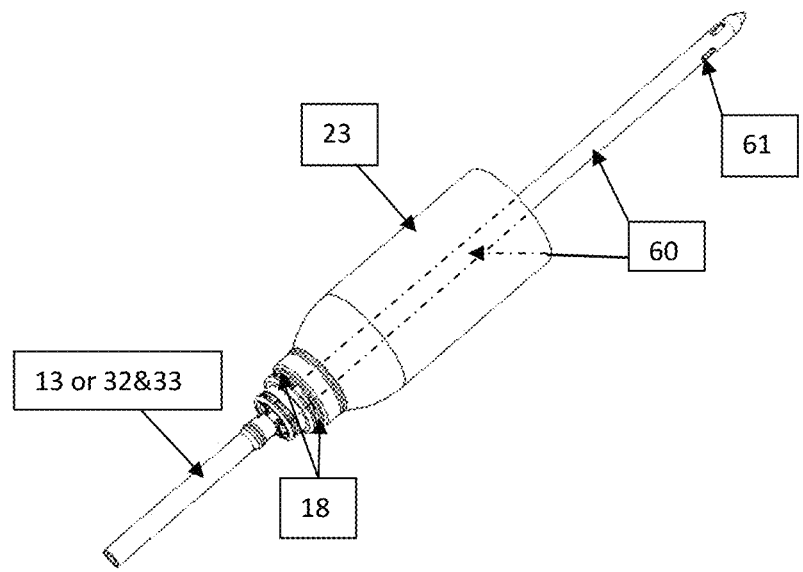
FIG. 20 is a side perspective view of the Indwelling Catheter used in both male and female combination embodiments with the Indwelling Catheter Connector attached completely inserted into the Hydro-Block Air Vent Condom Catheter with the Drain Tube attached.

FIGS. 18, 19 and 20 depict the Male Combination Catheter Embodiment with the Indwelling Catheter (60) being inserted and then fully inserted in the Condom (23) that comprises each of the four embodiments of the Hydro-Block Air Vent Condom Catheter (1)(2)(3) and (22).

FIGS. 21 and 22 depict the Female Combination Catheter Embodiment with the Indwelling Catheter (60) fully inserted in either the Pump Draining embodiment of the Hydro-Block Air Vent External Female Catheter (41) or the Gravity Draining embodiment of the Hydro-Block Air Vent External Female Catheter (42).

FIGS. 23 and 23A depict the components that are used in each embodiment that utilizes automatic urine detection and a pumping means which connect the urine collection assemblies to the pumping and storage means. These Figures depict the functionality of the Pressure Relief Balloon (31) before and after, as well as during, urination to prevent air lock or air bubble interference with the General Description of Reference Numerals in the Description and Drawings Any actual dimensions listed are those of the preferred embodiment. Actual dimensions or exact hardware details and means may vary in a final product or most preferred embodiment and should be considered means for so as not to narrow the claims of the patent.

List and Description of Component Parts of the Invention
(1) Inflatable Ring embodiment of the Hydro-Block Air Vent Condom Catheter
(2) Adhesive Ring embodiment of the Hydro-Block Air Vent Condom Catheter
(3) Storage Bag Venting embodiment of the Hydro-Block Air Vent Condom Catheter
(4) Storage Bag Hydro-Block Air Vent
(5) Storage Bag Discharge Tube
(6) Storage Bag
(7) Storage Bag Drain
(8) Storage Bar Drain Cap
(9) Storage Bag Coupler
(10) Inflatable Rings
(11) Hydro-Block Air Vent
(12) Drain Tube Attachment Node
(13) Drain Tube
(14) Hydro-Block Vent Retainer
(15) Hydro-Block Vent Retainer Air Holes
(16) Retro-Fit Assembly Drain Tube Attachment Node
(17) Retro-Fit Assembly Housing
(18) Retro-Fit Assembly Housing Air Holes
(19) Retro-Fit Hydro-Block Filter O-Rings
(20) Retro-Fit Hydro-Block Filter
(21) Retro-Fit Assembly
(22) Retro Fit Embodiment of the Hydro-Block Air Vent Condom Catheter
(23) Condom
(24) Adhesive Strips
(25) Drain Tube Coupler
(26) Inflatable Rings Port
(27) Compressed Air Source Valve
(28) Compressed Air Source
(29) Retro-Fit Urine Discharge Channel
(30) Pump and Sensor Connector
(31) Pressure Relief Balloon
(32) Liquid Hose
(33) Sensor Hose
(34) Quick Disconnect with Urine Sensor
(35) Interior Liquid Collection Area
(36) User Selected Pump Means
(37) Liquid Sensor
(41) Pump Draining embodiment of the Hydro-Block Air Vent External Female Catheter
(42) Gravity Draining embodiment of the Hydro-Block Air Vent External Female Catheter
(43) Body Contouring Sealing Sheet
(44) Hydro-block Air Intake Vent
(45) Hydrocolloid Adhesive
(46) Connector to Catheter Body Retainer
(47) Hydro-block Air Intake Coupler
(48) Interconnector Sealing O-Ring
(49) Quick Disconnect Coupling
(50) Pump Draining Drainage Hose
(51) Gravity Draining Drainage Hose
(52) External Catheter Molded Silicon Body
(53) Urine Passage Channel
(54) Micro Collection Chamber
(60) Indwelling Catheter
(61) Indwelling Catheter Urine Port
(62) Indwelling Catheter Connector
(63) Indwelling Catheter Connector Spacer Wings Detailed Description of the Preferred Embodiments 1) The Pump Draining Embodiment of the Hydro-Block Air Vent External Female Catheter with Quick Disconnect, Pump Connectivity and Automatic Urine Sensing for Pump Activation.

The Pump Draining embodiment of the Hydro-Block Air Vent External Female Catheter (41) depicted in FIGS. 1, 2A, 4, 23 and 23A is manufactured and comprised of the following components in their respective functional relationships:

The Pump Draining embodiment of the Hydro-Block Air Vent External Female Catheter (41) is formed in a size and shape capable of fitting between the legs and over the genitalia of a human female and forming a generally fluid tight seal around the vagina against the perineum, the mons pubis and the labia majora by securing the device thereto with a user selected attachment means, such as an adhesive means, garment or straps to complete the seal. As depicted in FIGS. 1, 2A, 23 and 23A the Pump Draining embodiment includes a quick disconnect system with pump connectivity and urine sensing to activate a pump comprised of a Pump and Sensor Connector (30), a Pressure Relief Balloon (31), a Liquid Hose (32), a Sensor Hose (33), a Urine Sensor (37) and a Quick Disconnect with Urine Sensor (34) or Quick Disconnect Coupling (49). This embodiment is manufactured and comprised of the following components in their respective functional relationships:

In the Pump Draining embodiment of the Hydro-Block Air Vent External Female Catheter (41) the device is held in place by the Hydrocolloid Adhesive (45) which the user places against her perineum, mons pubis and labia majora to form a relatively fluid tight seal thereby such that expelled urine will be captured by the device. The Hydrocolloid Adhesive (45) is attached to the Body Contouring Sealing Sheet (43) which in turn is attached to the External Catheter Molded Silicon Body (52) which is molded to form a catch basin or urinal Micro Collection Chamber (54). The Micro Collection Chamber (54) has a portion molded to form a hole there through designed to accept and hold in place by a fluid tight seal at least one Hydro-block Air Intake Vent (44). In FIGS. 1 and 2A the Micro Collection Chamber (54) has attached thereto at least one Urine Sensor (37) and/or a fluid sensor contained within the Quick Disconnect with Urine Sensor (34) as depicted in FIGS. 23 and 23A.

Upon urination the Urine Sensor (37) in FIGS. 1 and 2A, or the Quick Disconnect with Urine Sensor (34) detects the presence of the urine and by electronic means (radio, WiFi, direct cabling) the presence of urine is communicated to a pump or vacuum means which is then activated creating a suction within the Micro Collection Chamber (54) through the Liquid Hose (32) portion of the Pump Draining Drainage Hose (50) which is connected to the Micro Collection Chamber (54) by means of the Connector to Catheter Body Retainer (46) which is attached to a Hydro-block Air Intake Coupler (47) that maintains a fluid tight seal by means of a Interconnector Sealing O-Ring (48) to the Quick Disconnect Coupling (49) that is attached to the Pump Draining Drainage Hose (50) which is comprised of the Liquid Hose (32) and the Sensor Hose (33). In the direct cabling embodiment the Urine Sensor (37) or the Quick Disconnect with Urine Sensor (34) is connected to a User Selected Pumping Means (36) by wiring that passes through the Sensor Hose (33) to the Pump and Sensor Connector (30) which is further conductively connected in communication with the User Selected Pump Means (36).

Once a user has placed the device over her genitalia and it is attached to the user as heretofore described the user may pass urine into the device. During the process of urination gravity and excretion pressure from the user's bladder and urethra will cause the urine to flow into the Micro Collection Chamber (52) and then be drawn away from the genitalia by the activated pump or vacuum means through the Urine Passage Channel (53) and away from the user into a user selected collection or disposal means. The urine will not be able to accumulate around the genitalia because the Hydro-block Air Intake Vent (44) and the Hydro-block Air Intake Coupler (47) will provide free air flow into the device thereby causing the urine to completely drain away from the user's genitalia and ultimately discharge through the Liquid Hose (32) portion of the Pump Draining Drainage Hose (50) and into a user selected storage means.

The proper pumping and evacuation of the urine is facilitated by the Pressure Relief Balloon (31) which prevents air and fluid locks in the system that could prevent the proper pumping and/or draining of urine from the system. FIG. 23 depicts the Pressure Relief Balloon (31) in a collapsed state prior to the urination of a user. As depicted in FIGS. 23 and 23A the Pressure Relief Balloon (31) is inserted within the Liquid Hose (32) thereby becoming part of the Liquid Hose (32) permitting liquid to flow therethrough. The Pressure Relief Balloon (31) is composed of a material with elastic properties such as polyurethane. In order for the liquid sensors of the Liquid Sensor (37) or the Quick Disconnect with Urine Sensor (34) to activate the User Selected Pump Means (36) the Liquid Sensor (37) or the Quick Disconnect with Urine Sensor (34) must be in contact with the user's urine during a urination event. Once a user commences urination the force of the urination causes the urine to flow into the Liquid Hose (32) however the air in the Liquid Hose (32) and the air in the proximity of the Liquid Sensor (37) or the Quick Disconnect with Urine Sensor (34) prevent the Liquid Sensor (37) or the Quick Disconnect with Urine Sensor (34) from having adequate contact with the user's urine to activate the Liquid Sensor (37) or the Quick Disconnect with Urine Sensor (34) and thereby start the User Selected Pump Means (36). Once the user's urine passes into the Pressure Relief Balloon (31) portion of the Liquid Hose (32) the elastomeric properties of the Pressure Relief Balloon (31) provide an expandable and retractable vessel for the air that is being compressed by the urine flow as the Pressure Relief Balloon (31) begins to fill with urine such that sufficient air is forced out of the Liquid Hose (32) and the area surrounding the Liquid Sensor (37) or the Quick Disconnect with Urine Sensor (34) to permit the Liquid Sensor (37) or the Quick Disconnect with Urine Sensor (34) to have sufficient contact with the user's urine to be activated and in turn start the User Selected Pump Means (36). FIG. 23 depicts the Pressure Relief Balloon (31) in its collapsed state proper to a user's urination. FIG. 23A depicts the Pressure Relief Balloon (31) in its expanded state during a user's urination with about 60 ml of urine contained therein.

Once a user finishes urinating the Liquid Sensor (37) or the Quick Disconnect with Urine Sensor (34) will thereafter not sense the presence of urine since the user's urine is being drawn away by the User Selected Pump Means (36). The User Selected Pump Means (36) is programmed to continue sucking urine from the Liquid Hose (32) after the cessation of urination and deactivation of the Liquid Sensor (37) or the Quick Disconnect with Urine Sensor (34) for a sufficient period of time to evacuate the urine from the entire system and thereby restoring the Pressure Relief Balloon (31) to its pre-urination collapsed state. Once this evacuation cycle is complete the User Selected Pump Means (36) will shut off and stop pumping having pumped all the urine from the urination cycle of the user to a user selected storage means.

The Pump Draining embodiment of the Hydro-Block Air Vent External Female Catheter (41) may be manufactured from any suitably non-allergenic flexible material such as silicone rubber to optimize comfort to the user.

2) The Gravity Draining Embodiment of the Hydro-Block Air Vent External Female Catheter.

The Gravity Draining embodiment of the Hydro-Block Air Vent External Female Catheter (1) depicted in FIGS. 2, 3 and 5 is manufactured and comprised of the following components in their respective functional relationships:

The Gravity Draining embodiment of the Hydro-Block Air Vent External Female Catheter (42) is formed in a size and shape capable of fitting between the legs and over the genitalia of a human female and forming a generally fluid tight seal around the vagina against the perineum, the mons pubis and the labia majora by securing the device thereto with a user selected attachment means, such as an adhesive means, garment or straps to complete the seal. In the Gravity Draining embodiment of the Hydro-Block Air Vent External Female Catheter (42) the device is held in place by the Hydrocolloid Adhesive (45) which the user places against her perineum, mons pubis and labia majora to form a relatively fluid tight seal thereby such that expelled urine will be captured by the device. The Hydrocolloid Adhesive (45) is attached to the Body Contouring Sealing Sheet (43) which in turn is attached to the External Catheter Molded Silicon Body (52) which is molded to form a catch basin or urinal Micro Collection Chamber (54). The Micro Collection Chamber (54) has a portion molded to form a hole there through designed to accept and hold in place by a fluid tight seal at least one Hydro-block Air Intake Vent (44). When a user expels urine it is collected by gravity in the Micro Collection Chamber (54) and exits by gravity through the Urine Passage Channel (53) into the Gravity Draining Drainage Hose (13) which is connected to the Micro Collection Chamber (54) by means of the Connector to Catheter Body Retainer (6) which is attached to a Hydro-block Air Intake Coupler (47) that maintains a fluid tight seal by means of a Interconnector Sealing O-Ring (48) to the Quick Disconnect Coupling (49) that is attached to the Gravity Draining Drainage Hose (13).

Once a user has placed the device over her genitalia and it is attached to the user as heretofore described the user may pass urine into the device. During the process of urination gravity and excretion pressure from the user's bladder and urethra will cause the urine to flow into the Micro Collection Chamber (52) and then be drawn away from the genitalia by gravity through the Urine Passage Channel (53) and away from the user into a user selected collection or disposal means. The urine will not be able to accumulate around the genitalia because the Hydro-block Air Intake Vent (44) and the Hydro-block Air Intake Coupler (47) will provide free air flow into the device thereby causing the urine to completely drain away from the user's genitalia and ultimately discharge through the Gravity Draining Drainage Hose (13).

The Gravity Draining embodiment of the Hydro-Block Air Vent External Female Catheter (42) may be manufactured from any suitably non-allergenic flexible material such as silicone rubber to optimize comfort to the user.

3) The Inflatable Ring Embodiment of the Hydro-Block Air Vent Condom Catheter.

The Inflatable Ring embodiment of the Hydro-Block Air Vent Condom Catheter (1) depicted in FIG. 1 is manufactured and comprised of the following components in their respective functional relationships:

The Inflatable Ring embodiment of the Hydro-Block Air Vent Condom Catheter (1) is formed in a size and shape capable of fitting over a human penis and forming a fluid tight seal around the penis in general and the glans of the penis in particular. The Inflatable Ring embodiment of the Hydro-Block Air Vent Condom Catheter (1) is comprised of Hydro-Block Air Vent (11) material which permits air to enter into the Inflatable Ring embodiment of the Hydro-Block Air Vent Condom Catheter (1) while simultaneously preventing fluids from escaping therefrom. In the Inflatable Ring embodiment of the Hydro-Block Air Vent Condom Catheter (1) the device is held in place on the shaft of the penis proximally to the glans of the penis by an attachment means comprised of a plurality of Inflatable Rings (10), a Compressed Air Source (28), an Inflatable Rings Port (26) and Compressed Air Source Valve (27). The Inflatable Rings (10) are operatively connected to a Compressed Air Source (28) by means of an Inflatable Rings Port (26). The Compressed Air Source (28) delivers compressed air to the Inflatable Rings (10) through the Inflatable Rings Port (26) inflating thereby and forming a fluid tight seal against the user's penis. The Compressed Air Source (28) can remain attached throughout the use of the device or the user may close the Compressed Air Source Valve (27) thereby permitting the Inflatable Rings (10) to remain in an inflated condition if the user chooses to remove the Compressed Air Source (28) during use of the device. The Inflatable Ring embodiment of the Hydro-Block Air Vent Condom Catheter (1) is further comprised of a Drain Tube Attachment Node (12) which when the device is worn by a user is situated a small distance away from the distal end of the user's penis such that when urine is discharged from the distal end of the urethra urine can easily pass into the Interior Liquid Collection Area (35) and then through the Drain Tube Attachment Node (12) into a the Drain Tube (13) that is removably attached to the Drain Tube Attachment Node (12). Once a user has placed their penis inside the device and it is attached to the user as heretofore described the user may pass urine into the device. During the process of urination gravity and excretion pressure from the user's bladder and urethra will cause the urine to flow through the Drain Tube Attachment Node (12) and into the Drain Tube (13) and away from the user into a user selected collection or disposal means. The urine will not be able to accumulate around the glans or shaft of the penis because the Hydro-Block Air Vent (11) will provide free air flow into the device thereby causing the urine to completely drain away from the penis and ultimately discharge through the Drain Tube (13).

4) Adhesive Ring Embodiment of the Hydro-Block Air Vent Condom Catheter.

The Adhesive Ring embodiment of the Hydro-Block Air Vent Condom Catheter (2) depicted in FIG. 2 is manufactured and comprised of the following components in their respective functional relationships:

The Adhesive Ring embodiment of the Hydro-Block Air Vent Condom Catheter (2) is formed in a size and shape capable of fitting over a human penis and forming a fluid tight seal around the penis in general and the glans of the penis in particular. The Adhesive Ring embodiment of the Hydro-Block Air Vent Condom Catheter (2) is comprised of Hydro-Block Air Vent (11) material which permits air to enter into the Adhesive Ring embodiment of the Hydro-Block Air Vent Condom Catheter (2) while simultaneously preventing fluids from escaping therefrom. In the Adhesive Ring embodiment of the Hydro-Block Air Vent Condom Catheter (2) the device is held in place on the shaft of the penis proximally to the glans of the penis by an attachment means comprised of a plurality of Adhesive Strips (24). A user places their penis inside the device and adheres the device to the shaft of the penis proximally to the glans of the penis forming a fluid tight seal against the user's penis. The Adhesive Ring embodiment of the Hydro-Block Air Vent Condom Catheter (2) is further comprised of a Drain Tube Attachment Node (12) which when the device is worn by a user is situated a small distance away from the distal end of the user's penis such that when urine is discharged from the distal end of the urethra urine can easily pass into the Interior Liquid Collection Area (35) and then through the Drain Tube Attachment Node (12) into a the Drain Tube (13) that is removably attached to the Drain Tube Attachment Node (12). Once a user has placed their penis inside the device and it is attached to the user as heretofore described the user may pass urine into the device. During the process of urination gravity and excretion pressure from the user's bladder and urethra will cause the urine to flow through the Drain Tube Attachment Node (12) and into the Drain Tube (13) and away from the user into a user selected collection or disposal means. The urine will not be able to accumulate around the glans or shaft of the penis because the Hydro-Block Air Vent (11) will provide free air flow into the device thereby causing the urine to completely drain away from the penis and ultimately discharge through the Drain Tube (13).

5) Storage Bag Venting Embodiment of the Hydro-Block Air Vent Condom Catheter.

The Storage Bag Venting embodiment of the Hydro-Block Air Vent Condom Catheter (3) depicted in FIGS. 3 and 4 is manufactured and comprised of the following components in their respective functional relationships:

The Storage Bag Venting embodiment of the Hydro-Block Air Vent Condom Catheter (3) is formed in a size and shape capable of fitting over a human penis and forming a fluid tight seal around the penis in general and the glans of the penis in particular. The Storage Bag Venting embodiment of the Hydro-Block Air Vent Condom Catheter (3) is comprised of a Condom (23) having a user selected attachment means currently available with existing art condom catheters. In the Storage Bag Venting embodiment of the Hydro-Block Air Vent Condom Catheter (3) the device is held in place by means of the Condom (23) which is placed over the shaft of the penis proximally to the glans of the penis and attached thereto by the user selected attachment means currently available with existing art condom catheters. A user first places their penis inside the Condom (23) and then will adhere the device to the shaft of the penis proximally to the glans of the penis forming a fluid tight seal against the user's penis by the user selected attachment means currently available with existing art condom catheters. The Storage Bag Venting embodiment of the Hydro-Block Air Vent Condom Catheter (3) is further comprised of a Drain Tube Attachment Node (12) which when the device is worn by a user is situated a small distance away from the distal end of the user's penis such that when urine is discharged from the distal end of the urethra urine can easily pass into the Interior Liquid Collection Area (35) and then through the Drain Tube Attachment Node (12) into a the Drain Tube (13) that is removably attached to the Drain Tube Attachment Node (12). The Drain Tube (13) is further comprised of a Drain Tube Coupler (25) at the distal end of the Drain Tube (13) which permits the user to couple with a fluid tight seal the Drain Tube (13) to a Storage Bag Discharge Tube (5) such that when urine is discharged into the Condom (23) by a user the urine may freely pass without leakage through the Drain Tube Attachment Node (12), then into and through the Drain Tube (13), then into and through the Drain Tube Coupler (25), and then into and through the Storage Bag Discharge Tube (5) into a Storage Bag (6) by means of a fluid tight seal. The Storage Bag Discharge Tube (5) is further comprised of a Storage Bag Hydro-Block Air Vent (4). Once a user has placed their penis inside the device and it is attached to the user as heretofore described the user may pass urine into the device. During the process of urination gravity and excretion pressure from the user's bladder and urethra will cause the urine to flow through the Drain Tube Attachment Node (12) and into the Drain Tube (13) and away from the user into a user selected collection or disposal means. The urine will not be able to accumulate around the glans or shaft of the penis because the Storage Bag Hydro-Block Air Vent (4) will provide free air flow into the device thereby causing the urine to completely drain away from the penis and ultimately discharge through into the Storage Bag (6). The Storage Bag (6) in order to be reusable is further comprised of a Storage Bag Drain (8) that is fluid sealable by means of a Storage Bag Drain Cap (9).

6) The Retro Fit Embodiment of the Hydro-Block Air Vent Condom Catheter.

The Retro Fit Embodiment of the Hydro-Block Air Vent Condom Catheter (22) depicted in FIGS. 5, 6, 7 and 8 is manufactured and comprised of the following components in their respective functional relationships:

The Retro Fit Embodiment of the Hydro-Block Air Vent Condom Catheter (22) is generally comprised of three components: a Condom (23) having a user selected attachment means currently available with existing art condom catheters; a Retro-Fit Assembly (21); and a Drain Tube (13). In the Retro Fit Embodiment of the Hydro-Block Air Vent Condom Catheter (22) the device is held in place on the user's penis by means of the Condom (23) which is placed over the shaft of the penis proximally to the glans of the penis and attached thereto by the user selected attachment means currently available with existing art condom catheters. A user first places their penis inside the Condom (23) and then will adhere the device to the shaft of the penis proximally to the glans of the penis forming a fluid tight seal against the user's penis by the user selected attachment means currently available with existing art condom catheters. The Retro-Fit Assembly (21) is further comprised of: a Hydro-Block Vent Retainer (14), a plurality of Hydro-Block Vent Retainer Air Holes (15), a Retro-Fit Assembly Drain Tube Attachment Node (16), a Retro-Fit Assembly Housing (17), a plurality of Retro-Fit Assembly Housing Air Holes (18), at least two Retro-Fit Hydro-Block Filter O-Rings (19), a Retro-Fit Hydro-Block Filter (20) and a Retro-Fit Urine Discharge Channel (29). The Retro-Fit Assembly Housing (17) may be formed from any suitable material such as acetyl copolymer having disposed there through a Retro-Fit Urine Discharge Channel (29) that will permit user discharged urine to pass through and exit the Retro-Fit Assembly Housing (17) through the Retro-Fit Assembly Drain Tube Attachment Node (16) and into the Drain Tube (13) that is removably attached to the Retro-Fit Assembly Drain Tube Attachment Node (16). The Retro-Fit Assembly Housing (17) also has a plurality of Retro-Fit Assembly Housing Air Holes (18) that permit ambient air to freely flow from the outside of the Retro-Fit Assembly Housing (17) to the inside thereof. At least two Retro-Fit Hydro-Block Filter O-Rings (19) are removably attached forming a fluid tight seal between the Retro-Fit Hydro-Block Filter (20) and the Retro-Fit Assembly Housing (17) once the Hydro-Block Vent Retainer (14) is attached to the Retro-Fit Assembly Housing (17) by a snap fit or other suitable attachment means. The Retro-Fit Hydro-Block Filter O-Rings (19) also form a fluid tight seal between the Retro-Fit Urine Discharge Channel (29) and the Retro-Fit Assembly Housing Air Holes (18). The Retro-Fit Assembly Housing (17) is positioned in the distal end of the Condom (23) with the Drain Tube Attachment Node (16) and the Retro-Fit Assembly Housing Air Holes (18) protruding therefrom and exposed to ambient air, but otherwise forming a fluid tight seal with the Condom (23) such that discharged urine will not leak from the device but rather will pass out of the Condom (23) then into the Interior Liquid Collection Area (35) and then through the Retro-Fit Assembly (21) by means of the Retro-Fit Urine Discharge Channel (29) and then into the removably attached Drain Tube (13) and into a user selected collection or disposal means. Once the Retro Fit Embodiment of the Hydro-Block Air Vent Condom Catheter (22) is completely assembled and attached to a user and the user urinates, the expulsion force of urination and/or the force of gravity cause the urine to pass out of the Condom (23) then through the Retro-Fit Assembly (21) by means of the Retro-Fit Urine Discharge Channel (29) and then into the removably attached Drain Tube (13) and into a user selected collection or disposal means. The urine will completely drain by means of venting with ambient air that passes from the environment through the Retro-Fit Assembly Housing Air Holes (18) through a fluid tight channel formed by the Retro-Fit Hydro-Block Filter O-Rings (19) then through the Retro-Fit Hydro-Block Filter (20) and then through the Hydro-Block Vent Retainer Air Holes (15) of the Hydro-Block Vent Retainer (14) and into the Retro-Fit Urine Discharge Channel (29) thereby facilitating the complete drainage by venting of urine without leakage because of the fluid tight ventilation properties of the Retro-Fit Hydro-Block Filter (20).

7) The Modified Retro Fit Embodiment of the Hydro-Block Air Vent Condom Catheter with Quick Disconnect, Pump Connectivity and Automatic Urine Sensing for Pump Activation.

Figure 10:
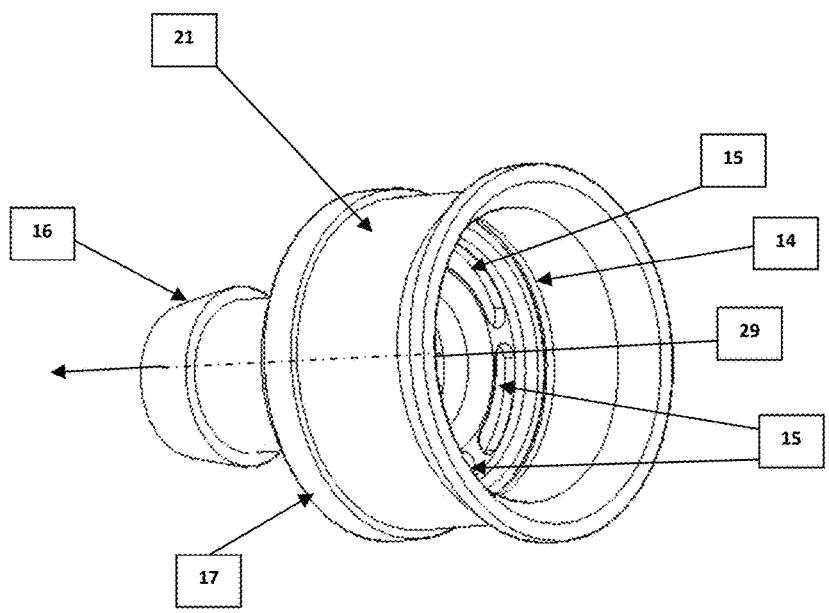
FIG. 10 is a proximal end perspective view of the Retro-Fit Assembly of the Retro-Fit Embodiment Hydro-Block Air Vent Condom Catheter.
Figure 11:
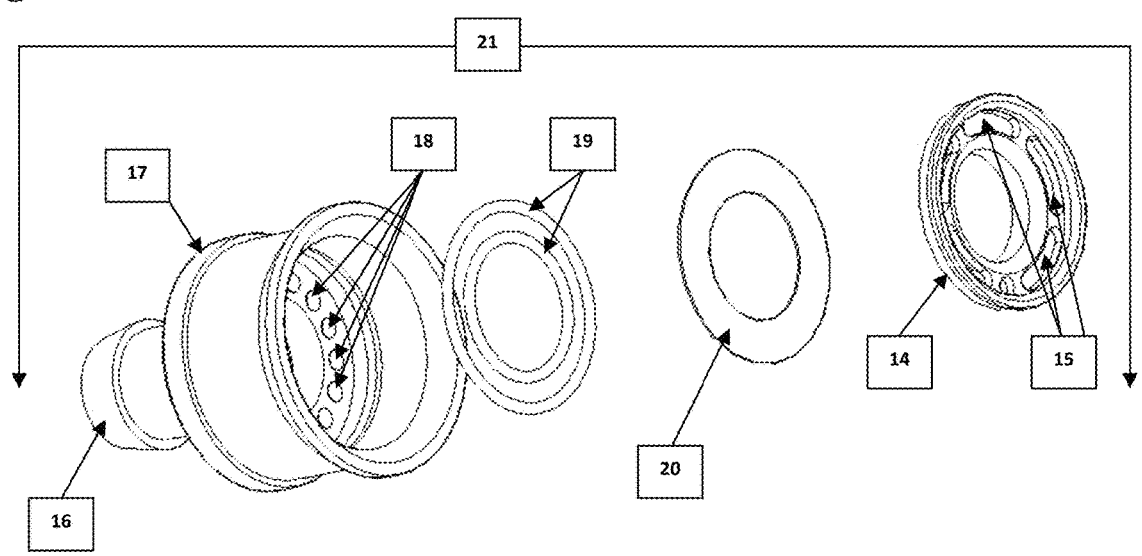
FIG. 11 is a proximal end exploded perspective view of the Retro-Fit Assembly of the Retro-Fit Embodiment Hydro-Block Air Vent Condom Catheter.
Figure 12:
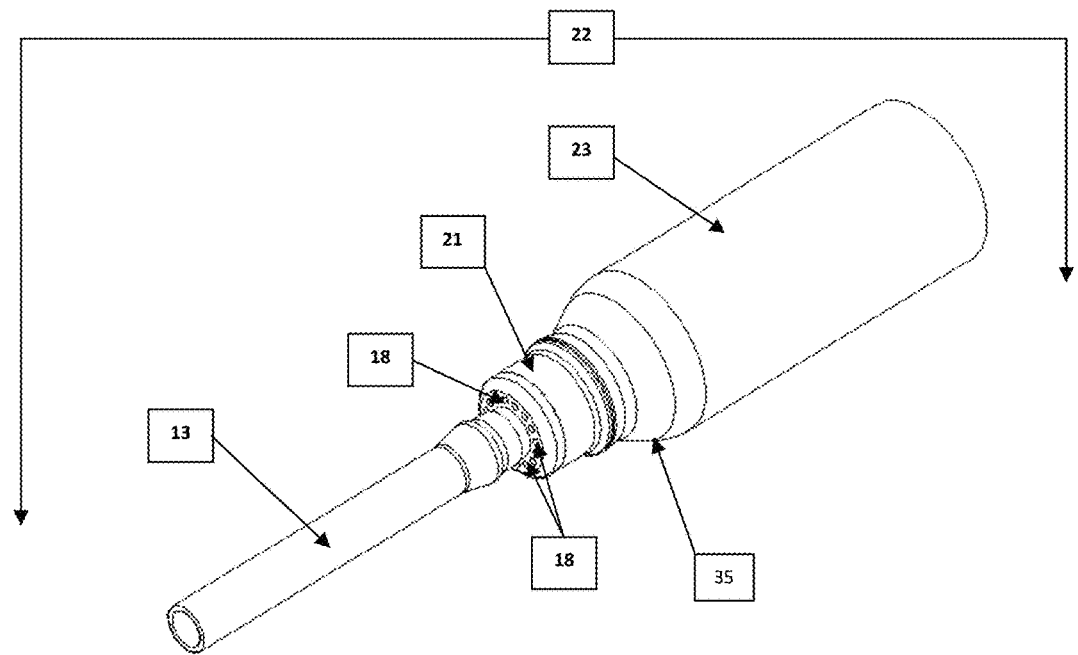
FIG. 12 is a distal end perspective view of the Retro-Fit Embodiment Hydro-Block Air Vent Condom Catheter.
Figure 13:
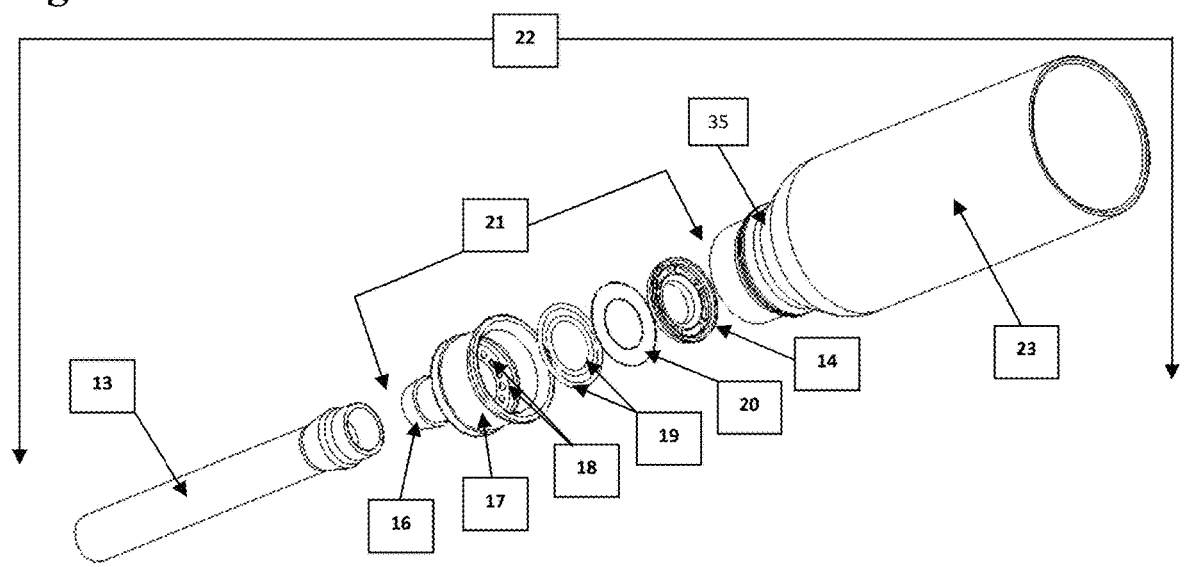
FIG. 13 is a proximal end exploded perspective view of the Retro-Fit Embodiment Hydro-Block Air Vent Condom Catheter.

The Retro Fit Embodiment of the Hydro-Block Air Vent Condom Catheter (22) depicted in FIGS. 5, 6, 7 and 8 has been modified as depicted in FIGS. 9, 10, 23 and 23A and wherein the Drain Tube (13) has been substituted with a quick disconnect system with pump connectivity and urine sensing to activate a pump comprised of a Pump and Sensor Connector (30), a Pressure Relief Balloon (31), a Liquid Hose (32), a Sensor Hose (33), and Quick Disconnect with Urine Sensor (34). This modified embodiment is manufactured and comprised of the following components in their respective functional relationships:

The Retro Fit Embodiment of the Hydro-Block Air Vent Condom Catheter (22) as depicted in FIGS. 7 and 8 has been modified as depicted in FIGS. 9 and 10 such that it is generally comprised of: a Condom (23) having a user selected attachment means currently available with existing art condom catheters; a Retro-Fit Assembly (21); a Pump and Sensor Connector (30); a Pressure Relief Balloon (31); a Liquid Hose (32); a Sensor Hose (33); and Quick Disconnect with Urine Sensor (34). In the modified Retro Fit Embodiment of the Hydro-Block Air Vent Condom Catheter (22) of FIGS. 7,8,9, and 10 the device is held in place on the user's penis by means of the Condom (23) which is placed over the shaft of the penis proximally to the glans of the penis and attached thereto by the user selected attachment means currently available with existing art condom catheters. A user first places their penis inside the Condom (23) and then will adhere the device to the shaft of the penis proximally to the glans of the penis forming a fluid tight seal against the user's penis by the user selected attachment means currently available with existing art condom catheters. The Retro-Fit Assembly (21) is further comprised of: a Hydro-Block Vent Retainer (14), a plurality of Hydro-Block Vent Retainer Air Holes (15), a Retro-Fit Assembly Drain Tube Attachment Node (16), a Retro-Fit Assembly Housing (17), a plurality of Retro-Fit Assembly Housing Air Holes (18), at least two Retro-Fit Hydro-Block Filter O-Rings (19), a Retro-Fit Hydro-Block Filter (20) and a Retro-Fit Urine Discharge Channel (29). The Retro-Fit Assembly Housing (17) may be formed from any suitable material such as acetyl copolymer having disposed there through a Retro-Fit Urine Discharge Channel (29) that will permit user discharged urine to pass into the Interior Liquid Collection Area (35) and then through and exit the Retro-Fit Assembly Housing (17) through the Retro-Fit Assembly Drain Tube Attachment Node (16) and into the Liquid Hose (32) that is removably attached to the Retro-Fit Assembly Drain Tube Attachment Node (16) by means of a Quick Disconnect with Urine Sensor (34). The Retro-Fit Assembly Housing (17) also has a plurality of Retro-Fit Assembly Housing Air Holes (18) that permit ambient air to freely flow from the outside of the Retro-Fit Assembly Housing (17) to the inside thereof. At least two Retro-Fit Hydro-Block Filter O-Rings (19) are removably attached forming a fluid tight seal between the Retro-Fit Hydro-Block Filter (20) and the Retro-Fit Assembly Housing (17) once the Hydro-Block Vent Retainer (14) is attached to the Retro-Fit Assembly Housing (17) by a snap fit or other suitable attachment means. The Retro-Fit Hydro-Block Filter O-Rings (19) also form a fluid tight seal between the Retro-Fit Urine Discharge Channel (29) and the Retro-Fit Assembly Housing Air Holes (18). The Retro-Fit Assembly Housing (17) is positioned in the distal end of the Condom (23) with the Drain Tube Attachment Node (16) and the Retro-Fit Assembly Housing Air Holes (18) protruding therefrom and exposed to ambient air, but otherwise forming a fluid tight seal with the Condom (23) such that discharged urine will not leak from the device but rather will pass out of the Condom (23) then through the Retro-Fit Assembly (21) by means of the Retro-Fit Urine Discharge Channel (29) and then into the removably attached Liquid Hose (32) that is removably attached to the Retro-Fit Assembly Drain Tube Attachment Node (16) by means of a Quick Disconnect with Urine Sensor (34) and into a user selected collection or disposal means. Once the modified Retro Fit Embodiment of the Hydro-Block Air Vent Condom Catheter (22) is completely assembled and attached to a user and the user urinates, the expulsion force of urination and/or the force of gravity cause the urine to pass out of the Condom (23) then through the Retro-Fit Assembly (21) by means of the Retro-Fit Urine Discharge Channel (29) and then into the removably attached Liquid Hose (32) that is attached by means of the Quick Disconnect with Urine Sensor (34) which senses the presence of urine and electronically communicates the presence of urine by means of the Pump and Sensor Connector (30) to a User Selected Pump Means (36) (such as the AMXD Max urine disposal pump) with collection or disposal means that is activated thereby and will evacuate the urine from the system and automatically shut off once the Quick Disconnect with Urine Sensor (34) no longer detects the presence of urine. The urine will completely drain by means of venting with ambient air that passes from the environment through the Retro-Fit Assembly Housing Air Holes (18) through a fluid tight channel formed by the Retro-Fit Hydro-Block Filter O-Rings (19) then through the Retro-Fit Hydro-Block Filter (20) and then through the Hydro-Block Vent Retainer Air Holes (15) of the Hydro-Block Vent Retainer (14) and into the Retro-Fit Urine Discharge Channel (29) thereby facilitating the complete drainage by venting of urine without leakage because of the fluid tight ventilation properties of the Retro-Fit Hydro-Block Filter (20).

The proper pumping and evacuation of the urine is facilitated by the Pressure Relief Balloon (31) which prevents air and fluid locks in the system that could prevent the proper pumping and/or draining of urine from the system. FIG. 23 depicts the Pressure Relief Balloon (31) in a collapsed state prior to the urination of a user. As depicted in FIGS. 23 and 23A the Pressure Relief Balloon (31) is inserted within the Liquid Hose (32) thereby becoming part of the Liquid Hose (32) permitting liquid to flow therethrough. The Pressure Relief Balloon (31) is composed of a material with elastic properties such as polyurethane. In order for the liquid sensors of the Liquid Sensor (37) or the Quick Disconnect with Urine Sensor (34) to activate the User Selected Pump Means (36) the Liquid Sensor (37) or the Quick Disconnect with Urine Sensor (34) must be in contact with the user's urine during a urination event. Once a user commences urination the force of the urination causes the urine to flow into the Liquid Hose (32) however the air in the Liquid Hose (32) and the air in the proximity of the Liquid Sensor (37) or the Quick Disconnect with Urine Sensor (34) prevent the Liquid Sensor (37) or the Quick Disconnect with Urine Sensor (34) from having adequate contact with the user's urine to activate the Liquid Sensor (37) or the Quick Disconnect with Urine Sensor (34) and thereby start the User Selected Pump Means (36). Once the user's urine passes into the Pressure Relief Balloon (31) portion of the Liquid Hose (32) the elastomeric properties of the Pressure Relief Balloon (31) provide an expandable and retractable vessel for the air that is being compressed by the urine flow as the Pressure Relief Balloon (31) begins to fill with urine such that sufficient air is forced out of the Liquid Hose (32) and the area surrounding the Liquid Sensor (37) or the Quick Disconnect with Urine Sensor (34) to permit the Liquid Sensor (37) or the Quick Disconnect with Urine Sensor (34) to have sufficient contact with the user's urine to be activated and in turn start the User Selected Pump Means (36). FIG. 23 depicts the Pressure Relief Balloon (31) in its collapsed state proper to a user's urination. FIG. 23A depicts the Pressure Relief Balloon (31) in its expanded state during a user's urination with about 60 ml of urine contained therein.

Once a user finishes urinating the Liquid Sensor (37) or the Quick Disconnect with Urine Sensor (34) will thereafter not sense the presence of urine since the user's urine is being drawn away by the User Selected Pump Means (36). The User Selected Pump Means (36) is programmed to continue sucking urine from the Liquid Hose (32) after the cessation of urination and deactivation of the Liquid Sensor (37) or the Quick Disconnect with Urine Sensor (34) for a sufficient period of time to evacuate the urine from the entire system and thereby restoring the Pressure Relief Balloon (31) to its pre-urination collapsed state. Once this evacuation cycle is complete the User Selected Pump Means (36) will shut off and stop pumping having pumped all the urine from the urination cycle of the user to a user selected storage means.

As depicted in FIGS. 14 and 15, the sensing of liquid can also be located in the condom by means of a Liquid Sensor (37). All of the fluid sensors of this invention can communicate with a pumping means either directly by conductive wire or by wireless transmission.

7) Male Combination Catheter Embodiment

When a male user is in need of bladder management for urinary retention or ischuria he selects an Indwelling Catheter (60) of adequate length to reach up into his bladder through the urethra such that the Indwelling Catheter Ports (61) are inside the bladder and the opposite end extending a sufficient distance from the end of his penis to facilitate a connection to a user selected condom catheter utilizing hydro-block technology from the four embodiments above listed. Additionally the selected Indwelling Catheter (60) ideally should have an outside diameter that is smaller than the diameter of the urethra such that the Indwelling Catheter (60) can easily be inserted through the urethra with minimal friction or resistance from the inner wall of the urethra. The user then places and attaches the user selected condom catheter utilizing hydro-block technology from the four embodiments above listed on his penis using the method and component parts as described above in the four condom catheter embodiments utilizing hydro-block technology. Once the user selected condom catheter utilizing hydro-block technology from the four embodiments above is in place on the user's penis the user then inserts the end of the Indwelling Catheter (60) with the Indwelling Catheter Ports (61) through the selected condom catheter opening next to the tip of the penis and then into the urethral opening at the tip of the penis, through the length of the urethra and into the user's bladder such that the Indwelling Catheter Ports (61) are inside the bladder. The Indwelling Catheter (60) is then connected to the user selected condom catheter by means of a Indwelling Catheter Connector (62) attached to the Indwelling Catheter (60) which is automatically centered in the user selected condom catheter by means of Indwelling Catheter Connector Spacer Wings (63). The user then connects the selected condom catheter utilizing hydro-block technology from the four embodiments above to the corresponding hose assembly as depicted with each of the embodiments which in turn is attached to a urine collection means. The device in this embodiment is now ready for use.

Alternatively the Indwelling Catheter (60) may be inserted into the user's bladder first and then attached to the selected condom catheter utilizing hydro-block technology from the four embodiments above which is later put on by the user.

8) Female Combination Catheter Embodiment

When a female user is in need of bladder management for urinary retention or ischuria she selects an Indwelling Catheter (60) of adequate length to reach up into her bladder through the urethra such that the Indwelling Catheter Ports (61) are inside the bladder and the opposite end extending a sufficient distance from the end of her vaginal opening of her urethra to facilitate a connection to a user selected Hydro-Block Air Vent External Female Catheter from the two embodiments above listed. Additionally the selected Indwelling Catheter (60) ideally should have an outside diameter that is smaller than the diameter of the urethra such that the Indwelling Catheter (60) can easily be inserted through the urethra with minimal friction or resistance from the inner wall of the urethra. The user then places and attaches the user selected Hydro-Block Air Vent External Female Catheter from the two embodiments above listed over her genitalia using the method and component parts as described above in the two Hydro-Block Air Vent External Female Catheter embodiments above listed. Once the user selected Hydro-Block Air Vent External Female Catheter from the two embodiments above listed is in place over the user's genitalia the user then inserts the end of the Indwelling Catheter (60) with the Indwelling Catheter Ports (61) through the selected Hydro-Block Air Vent External Female Catheter opening next to the vaginal end of the urethra and then into the urethral opening, through the length of the urethra and into the user's bladder such that the Indwelling Catheter Ports (61) are inside the bladder. The Indwelling Catheter (60) is then connected to the user selected Hydro-Block Air Vent External Female Catheter by means of a Indwelling Catheter Connector (62) attached to the Indwelling Catheter (60) which is automatically centered in the user selected Hydro-Block Air Vent External Female Catheter by means of Indwelling Catheter Connector Spacer Wings (63). The user then connects the selected Hydro-Block Air Vent External Female Catheter from the two embodiments above listed to the corresponding hose assembly as depicted with each of the embodiments which in turn is attached to a urine collection means. The device in this embodiment is now ready for use.

Alternatively the Indwelling Catheter (60) may be inserted into the user's bladder first and then attached to the selected Hydro-Block Air Vent External Female Catheter from the two embodiments above listed which is later put on by the user.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. Accordingly, the scope of the invention should be determined not by the embodiments illustrated, but by the claims and their legal equivalents which accompany this application.

Having described my invention, I claim:

1. A hydro-block air vent combination catheter system comprised of:
   an external catheter selected from the group consisting of:
      a condom catheter or a catheter capable of covering the female genitalia and containing urine therein;
   an external catheter attachment means attached to the external catheter;

an indwelling catheter attachment means attached to the external catheter such that the hydro-block air vent combination catheter system can be used by a user with either the external catheter alone or in combination with an indwelling catheter attached to the external catheter;

a liquid sensor;

a liquid hose;

a pressure relief balloon capable of regulating liquids in the liquid hose such that the liquid sensor will detect the presence of liquids without air bubble interference;

a liquid blocking air vent attached to the external catheter wherein the liquid blocking air vent permits ambient air to enter into or escape from the external catheter and prevents liquid from escaping from within the external catheter; and a collection means attached to the external catheter wherein the collection means facilitates the passage of urine from the external catheter to a user selected disposal means;

the collection means is comprised of a pump and sensor connector wherein the pump and sensor connector is capable of being connected to a user selected pump, wherein the collection means is attached to the external catheter by the external catheter attachment means thereby permitting a user's urine to: pass out of the external catheter; be detected by the liquid sensor thereby electronically transmitting data regarding the presence of the user's urine to the pump and sensor connector through the sensor hose thereby facilitating the activation of the user selected pump which when attached and activated draws urine away from the external catheter exiting the external catheter into the liquid hose, then through the pump and sensor connector and then through the user selected pump to a user selected disposal means.

2. The hydro-block air vent combination catheter system of claim 1 wherein the liquid sensor is located in the external catheter such that it will sense the presence of a user's urine upon urination.

3. A method of using the hydro-block air vent combination catheter system of claim 1 consisting of the steps of:
selecting the external catheter;
attaching the external catheter on the user's body for use by the external catheter attachment means;
positioning the collection means to facilitate a flow of urine from the external catheter to the disposal means;
selecting a pump;
connecting the pump to the pump and sensor connector; and
turning the pump on such that when the liquid sensor detects the presence of the user's urine the pump will turn on and draw the urine away from the condom through the liquid hose then through the pump to be discharged in the user selected disposal means.

4. A hydro-block air vent combination catheter system comprised of:
an external catheter selected from the group consisting of: a condom catheter or a catheter capable of covering the female genitalia and containing urine therein;
an external catheter attachment means attached to the external catheter;
an indwelling catheter attachment means attached to the external catheter such that the hydra-block air vent combination catheter system can be used by a user with either the external catheter alone or in combination with an indwelling catheter attached to the external catheter:
the indwelling catheter attachment means is comprised of:
a locking mechanism that permits a user to snap into place or remove an indwelling catheter;
the locking mechanism being further comprised of a multiplicity of spacers that will maintain the indwelling catheter in a position that urine may also pass around the indwelling catheter as well as through the indwelling catheter during user;
a liquid sensor;
a liquid hose;
a pressure relief balloon capable of regulating liquids in the liquid hose such that the liquid sensor will detect the presence of liquids without air bubble interference;
a liquid blocking air vent attached to the external catheter wherein the liquid blocking air vent permits ambient air to enter into or escape from the external catheter and prevents liquid from escaping from within the external catheter; and
a collection means attached to the external catheter wherein the collection means facilitates the passage of urine from the external catheter to a user selected disposal means.

5. The hydro-block air vent combination catheter system of claim 4 wherein the collection means is comprised of:
a drain tube attached to the external catheter; and
a storage bag attached to the drain tube wherein urine being discharged by a user will pass out of the external catheter into the drain tube and then pass into the storage bag.

6. The hydro-block air vent combination catheter system of claim 5 wherein the drain tube is further comprised of:
a liquid blocking air vent attached to the drain tube wherein the liquid blocking air vent permits ambient air to enter into or escape from the drain tube and prevents liquid from escaping from within the drain tube.

7. A method of using the hydro-block air vent combination catheter system of claim 4 consisting of the steps of:
selecting the external catheter;
attaching the external catheter on the user's body for use by the external catheter attachment means;
positioning the collection means to facilitate a flow of urine from the external catheter to the disposal means.

8. A method of using the hydro-block air vent combination catheter system of claim 4 consisting of the steps of:
selecting the external catheter;
attaching the external catheter on the user's body for use by the external catheter attachment means;
inserting an indwelling catheter into the bladder of the user;
attaching the indwelling catheter to the external catheter; and
positioning the collection means to facilitate a flow of urine from the external catheter to the disposal means.

* * * * *